(12) United States Patent
Godwin

(10) Patent No.: US 11,027,022 B2
(45) Date of Patent: *Jun. 8, 2021

(54) CONJUGATES AND CONJUGATING REAGENTS

(71) Applicant: POLYTHERICS LIMITED, Cambridge (GB)

(72) Inventor: Antony Godwin, London (GB)

(73) Assignee: POLYTHERICS LIMITED, Cambridge (GB)

(*) Notice: Subject to any disclaimer, the term of this patent is extended or adjusted under 35 U.S.C. 154(b) by 79 days.

This patent is subject to a terminal disclaimer.

(21) Appl. No.: 16/097,864

(22) PCT Filed: May 19, 2017

(86) PCT No.: PCT/GB2017/051407
§ 371 (c)(1),
(2) Date: Oct. 31, 2018

(87) PCT Pub. No.: WO2017/199046
PCT Pub. Date: Nov. 23, 2017

(65) Prior Publication Data
US 2019/0134220 A1    May 9, 2019

(30) Foreign Application Priority Data
May 20, 2016 (GB) ...................... 1608936

(51) Int. Cl.
*A61K 47/69* (2017.01)
*A61K 47/68* (2017.01)
*A61K 31/404* (2006.01)
*A61K 31/5365* (2006.01)

(52) U.S. Cl.
CPC ........ *A61K 47/6951* (2017.08); *A61K 31/404* (2013.01); *A61K 31/5365* (2013.01); *A61K 47/6817* (2017.08); *A61K 47/6849* (2017.08); *A61K 47/6889* (2017.08)

(58) Field of Classification Search
None
See application file for complete search history.

(56) References Cited

U.S. PATENT DOCUMENTS

| | | | |
|---|---|---|---|
| 5,068,227 A | 11/1991 | Weinshenker | |
| 2001/0034333 A1 | 10/2001 | Kosak | |
| 2011/0178287 A1 | 7/2011 | Glucksmann et al. | |
| 2012/0302505 A1* | 11/2012 | Fetzer | A61K 38/08 514/15.4 |

FOREIGN PATENT DOCUMENTS

| | | |
|---|---|---|
| EP | 2260873 A1 | 12/2010 |
| WO | 9002141 A1 | 3/1990 |
| WO | 9113100 A1 | 9/1991 |
| WO | 2004060965 A2 | 7/2004 |
| WO | 2005007197 A2 | 1/2005 |
| WO | 2009001364 A2 | 12/2008 |
| WO | 2009047500 A1 | 4/2009 |
| WO | 2009152440 A1 | 12/2009 |
| WO | 2010100430 A1 | 9/2010 |
| WO | 2012145632 A1 | 10/2012 |
| WO | 2013190272 A1 | 12/2013 |
| WO | 2014064423 A1 | 5/2014 |
| WO | 2014064424 A1 | 5/2014 |
| WO | 2015189478 A1 | 12/2015 |
| WO | 2016059377 A1 | 4/2016 |
| WO | 2016063006 A1 | 4/2016 |

OTHER PUBLICATIONS

International Search Report and Written Opinion issued in corresponding International Patent Application No. PCT/GB2017/051407 dated Aug. 4, 2017 (10 pages).
Del Rosario et al., "Sulfhydryl Site-Specific Cross-Linking and Labeling of Monoclonal Antibodies by a Fluorescent Equilibrium Transfer Alkylation Cross-Link Reagent," Bioconjugate Chemistry, 1990, vol. 1, No. 1, pp. 51-59.
Khalili et al., "Comparative Binding of Disulfide-Bridged PEG-Fabs," Bioconjugate Chemistry, 2012, vol. 23, No. 11, pp. 2262-2277.
Liberatore et al., "Site-Directed Chemical Modification and Cross-Linking of a Monoclonal Antibody Using Equilibrium Transfer Alkylating Cross-Link Reagents," Bioconjugate Chemistry, 1990, vol. 1, No. 1, pp. 36-50 (12 pages).

(Continued)

*Primary Examiner* — Bong-Sook Baek
(74) *Attorney, Agent, or Firm* — Kilyk & Bowersox, P.L.L.C.

(57) ABSTRACT

A conjugate of a protein or peptide conjugated to a therapeutic, diagnostic or labelling agent via a linker, in which the linker includes a protein or peptide bonding portion having the general formula:

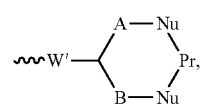

(I)

in which Pr represents said protein or peptide, each Nu represents a nucleophile present in or attached to the protein or peptide, each of A and B independently represents a $C_{1-4}$alkylene or alkenylene chain, and W' represents an electron withdrawing group or a group obtained by reduction of an electron withdrawing group; and in which the linker also includes a cyclodextrin. The invention also provides reagents for making such conjugates.

13 Claims, 2 Drawing Sheets

(56) References Cited

OTHER PUBLICATIONS

Lyon et al., "Reducing hydrophobicity of homogeneous antibody-drug conjugates improves pharmacokinetics and therapeutic index," Nature Biotechnology, 2015, vol. 33, No. 7, pp. 733-735 (4 pages).

* cited by examiner

CONJUGATES AND CONJUGATING REAGENTS

This application is a National Stage Application of PCT/GB2017/051407, filed May 19, 2017, which claims priority to United Kingdom Patent Application No. 1608936.9, filed May 20, 2016.

FIELD OF INVENTION

This invention relates to novel conjugates and novel conjugating reagents.

BACKGROUND OF THE INVENTION

Much research has been devoted in recent years to the conjugation of a wide variety of payloads, for example therapeutic, diagnostic and labelling agents, to peptides and proteins for a wide range of applications. The protein or peptide itself may have therapeutic properties, and/or it may be a binding protein.

Peptides and proteins have potential use as therapeutic agents, and conjugation is one way of improving their properties. For example, water soluble, synthetic polymers, particularly polyalkylene glycols, are widely used to conjugate therapeutically active peptides or proteins. These therapeutic conjugates have been shown to alter pharmacokinetics favourably by prolonging circulation time and decreasing clearance rates, decreasing systemic toxicity, and in several cases, displaying increased clinical efficacy. The process of covalently conjugating polyethylene glycol, PEG, to proteins is commonly known as "PEGylation". The PEG chain may carry a payload, for example a therapeutic, diagnostic or labelling agent. Alternative polymers to PEG have been proposed, but PEG remains the predominant polymer of choice.

Binding proteins, particularly antibodies or antibody fragments, are frequently conjugated. The specificity of binding proteins for specific markers on the surface of target cells and molecules has led to their extensive use either as therapeutic or diagnostic agents in their own right or as carriers for payloads which may include therapeutic, diagnostic or labelling agents. Such proteins conjugated to labels and reporter groups such as fluorophores, radioisotopes and enzymes find use in labelling and imaging applications, while conjugation to drugs such as cytotoxic agents and chemotherapy drugs to produce antibody-drug conjugates (ADCs) allows targeted delivery of such agents to specific tissues or structures, for example particular cell types or growth factors, minimising the impact on normal, healthy tissue and significantly reducing the side effects associated with chemotherapy treatments. Such conjugates have extensive potential therapeutic applications in several disease areas, particularly in cancer.

Many methods of conjugating proteins and peptides have been reported in the literature. Probably the most commonly used process involves the use of conjugating reagents based on maleimides. Such reagents are described in many publications, for example WO 2004/060965. An alternative approach which leads to more homogeneous products is described by Liberatore et al, Bioconj. Chem 1990, 1, 36-50, and del Rosario et al, Bioconj. Chem. 1990, 1, 51-59, which describe the use of reagents which may be used to cross-link across the disulfide bonds in proteins, including antibodies. WO 2005/007197 describes a process for the conjugation of polymers to proteins, using novel conjugating reagents having the ability to conjugate with both sulfur atoms derived from a disulfide bond in a protein to give novel thioether conjugates, while WO 2009/047500 describes the use of the same conjugating reagents to bond to polyhistidine tags attached to the protein. WO 2010/100430 describes reagents capable of forming a single carbon bridge across the disulfide bond in a protein. Other documents relating to the conjugation of proteins include WO 2014/064423, WO 2013/190292, WO 2013/190272 and EP 2260873.

WO 2014/064424 describes specific ADCs in which the drug is a maytansine and the antibody is bonded by cross-linking across a disulfide bond. WO 2014/064423 describes specific ADCs in which the drug is an auristatin and the antibody is bonded by cross-linking across a disulfide bond. The linkers illustrated in the Examples of these documents contain a PEG portion in which one end of the PEG chain is attached via a further portion of the linker to the drug, while the other end of the PEG chain is attached via a further portion of the linker to the antibody. This is a common structural pattern for ADCs.

Over recent years, the importance of the linker which links a payload to the protein or peptide in a conjugate, has become apparent. Often, the key decision to be taken is whether it is desired to have a cleavable linker, i.e. a linker which, on administration of the conjugate, degrades to release the free payload, or a non-cleavable linker. Another key decision is whether or not to include PEG in the linker. Subject to these considerations, in principle, any linker may be used. In practice, however, changes in structure of the linker may lead to differences in the properties either of the conjugating reagent or of the resulting conjugate.

Cyclodextrins are cyclic oligosaccharides, made from 5 or more glucose ($\alpha$-D-glucopyranoside) units bound together in a ring, typically linked by their 1 and 4 positions. The most common cyclodextrins are $\alpha$, $\beta$ and $\gamma$, which are 6, 7 and 8 membered rings respectively. The structure of cyclodextrins has been determined and may be described as a toroid or a barrel, with one end slightly narrower than the other. This structure provides an apolar cavity in which less hydrophilic molecules can reside, protected from the external milieu by the hydrophilic shell of the cyclodextrin, which assists in solubilising the less hydrophilic molecule in water. The bonding of the guest molecule to the cyclodextrin in such complexes is generally non-covalent, and cyclodextrin-drug complexes are often referred to as 'inclusion complexes' where the cyclodextrin 'host' molecule holds the 'guest' drug molecule in a non-covalent interaction. As a result of the ability to form complexes, cyclodextrin and cyclodextrin derivatives have been used extensively as excipients within pharmaceutical preparations.

Alternatively, but less commonly, cyclodextrins have been reacted with active ingredients to form covalent conjugates. WO 91/13100 describes cyclodextrin covalently attached to a targeting carrier, which may be an antibody or fragment thereof. WO 90/02141 discloses cyclodextrins covalently bonded to agents such as pharmaceuticals. US2001/0034333 discusses the difficulties of using individual monomeric cyclodextrins, and proposes the use of cross-linked cyclodextrin polymers to solve these problems. It describes a fluorescent payload covalently linked to a cross-linked cyclodextrin polymer, which was subsequently conjugated to an antibody using an NHS ester functionality.

We have now found that incorporation of cyclodextrins into conjugates of a particular structure gives surprisingly effective results. These conjugates are surprisingly potent in vivo.

SUMMARY OF THE INVENTION

The invention provides a conjugate of a protein or peptide conjugated to a therapeutic, diagnostic or labelling agent via a linker, in which the linker includes a protein or peptide bonding portion having the general formula:

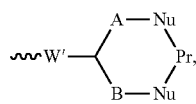

(I)

in which Pr represents said protein or peptide, each Nu represents a nucleophile present in or attached to the protein or peptide, each of A and B independently represents a $C_{1-4}$alkylene or alkenylene chain, and W' represents an electron withdrawing group or a group obtained by reduction of an electron withdrawing group; and in which the linker also includes a cyclodextrin.

The invention also provides a conjugating reagent capable of reacting with a protein or peptide, and including a therapeutic, diagnostic or labelling agent and a linker which includes a functional group capable of reacting with a protein or peptide, said functional group being a group of the formula:

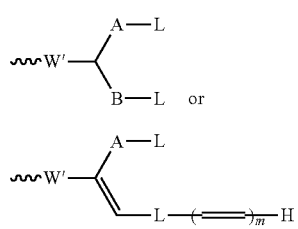

in which W represents an electron withdrawing group, A and B have the meanings given above, m is 0 to 4, and each L independently represents a leaving group; and in which the linker also includes a cyclodextrin.

The invention also provides a process for the preparation of a conjugate according to the invention, which comprises reacting a protein or peptide with a conjugating reagent according to the invention.

DETAILED DESCRIPTION OF THE INVENTION

The conjugates of the invention include a therapeutic, diagnostic or labelling agent (the payload) covalently linked to a protein or peptide via a linker, while the reagents of the invention include the payload covalently linked to the functional group of formula II or II' capable of reacting with a protein or peptide (the protein binding portion). The cyclodextrin in the conjugate or reagent of the invention may be present within the backbone of the linker, or it may be present as a pendant group which is tethered to the backbone of the linker.

Conjugates having the former structure may be represented schematically by the formula D~CD~F', in which D represents the therapeutic, diagnostic or labelling agent, F' represents the group of formula I, and CD represent a cyclodextrin, while reagents having the corresponding structure may be represented schematically by the formula D~CD~F, in which D represents the therapeutic, diagnostic or labelling agent, F represents the group of formula II or II', and CD represent a cyclodextrin. Preferably however the conjugates and reagents of the invention have the latter structure, i.e. the cyclodextrin is present as a pendant group which is tethered to the backbone of the linker. A conjugate of the invention having this structure may be represented schematically by the formula:

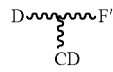

in which D represents the therapeutic, diagnostic or labelling agent, F' represents the group of formula I, and CD represents a cyclodextrin, while the reagent of the invention may be represented schematically by the formula:

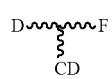

in which D represents the therapeutic, diagnostic or labelling agent, F represents the group of formula II or II', and CD represents a cyclodextrin. The functional grouping F is capable of reacting with two nucleophiles present in a protein or peptide as explained below.

The Cyclodextrin

Cyclodextrins are cyclic oligomers of α-D-glucopyranoside units. The cyclic glucose units are bound together at their 1,4-positions. Rings of various sizes are possible, the most common being α-cyclodextrin, which has 6 sugar moieties within the ring; β-cyclodextrin, which has 7 sugar moieties within the ring; and γ-cyclodextrin, which has 8 sugar moieties within the ring. These cyclodextrins are naturally occurring, and are shown below:

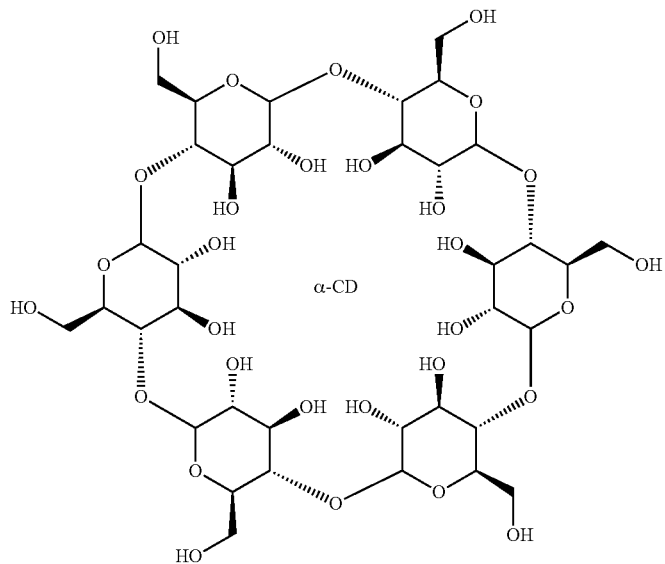

α-CD

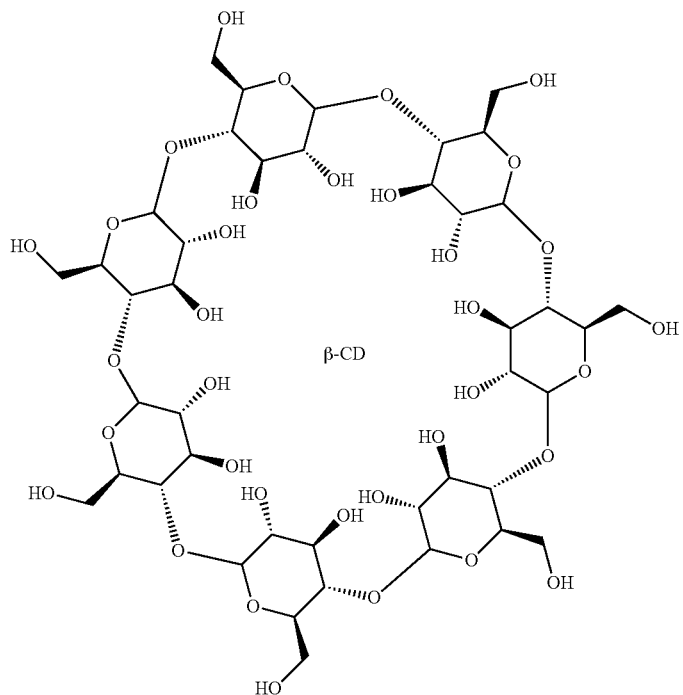

β-CD

-continued

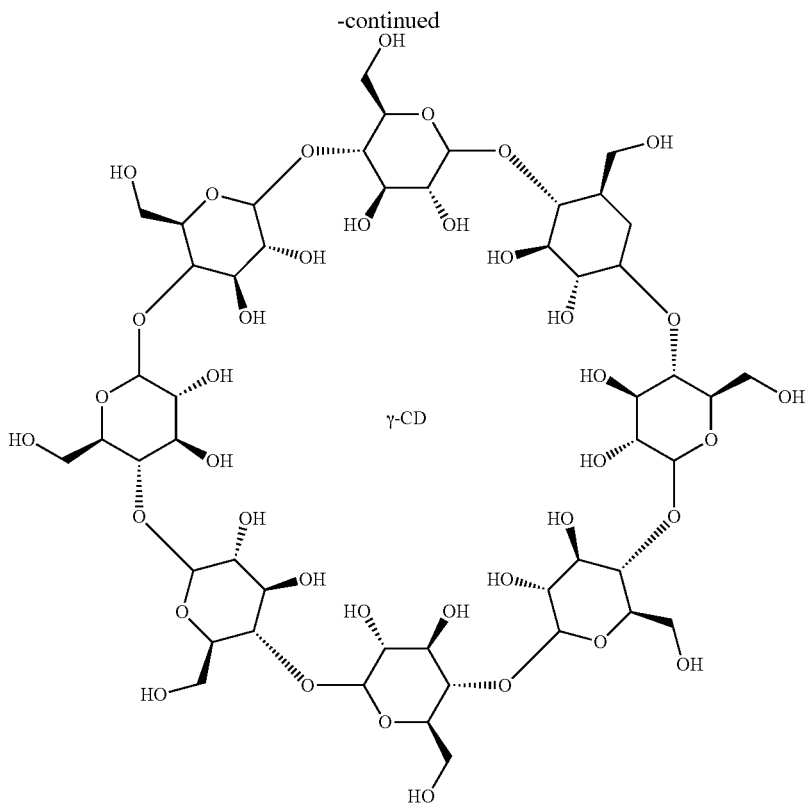

γ-CD

Other cyclodextrins with different ring sizes may be prepared synthetically or enzymatically by known methods, for example as described by Endo & Ueda, FABAD J. Pharm. Sci., 2004, 29, 27-38. In one embodiment of the invention, the cyclodextrin is α-cyclodextrin; in another embodiment, the cyclodextrin is β-cyclodextrin; and in another embodiment the cyclodextrin is γ-cyclodextrin.

The cyclodextrin may be monocyclic (i.e. composed of a single cyclodextrin ring), or two or more cyclodextrin rings forming a cyclodextrin dimer or polymer may be present. Cyclodextrin dimers and polymers are known, and may be synthesised by known methods. Preferably the cyclodextrin is monocyclic.

Each cyclic glucose unit in a native cyclodextrin carries three hydroxy groups, two of which are in the 2 and 3 positions and are carried directly by the glucose ring and one of which is in the 6 position and is part of a hydroxymethyl group. One or more of these may be replaced by any other desired group to form a derivatised cyclodextrin. Such derivatised cyclodextrins should be understood to be within the scope of the present invention. For example, a hydroxy group may be replaced by a halogen atom; or a hydroxy group may be replaced by a group of formula —YR$^b$, wherein Y represents —O—, —S—, —O—CO—, —CO—O—, —CO—NR$^b$—, —NR$^b$—CO—, —CO—, —SO—, —SO$_2$—, —S—CO—, —CO—S—, —N=CR$^b$—, —CH=N—R$^b$, —O—CO—O—, —O—SO$_2$—, —SO$_2$—O—, or —O—SO$_2$—O—, and R$^b$ represents a hydrogen atom or an alkyl (preferably C$_{1-6}$ alkyl, for example methyl), alkenyl (preferably C$_{2-6}$ alkenyl), alkynyl (preferably C$_{2-6}$ alkynyl, for example propargyl), aryl (preferably phenyl), or alkyl-aryl (preferably C$_{1-6}$alkylphenyl) group, each of which may be unsubstituted or substituted by one or more hydroxy groups; or a hydroxy group may be replaced by a group of formula —R$^b$, —NR$^b$R$^b$, =NR$^b$, —SiR$^b$R$^b$R$^b$, —O—SiR$^b$R$^b$R$^b$, —PR$^b$R$^b$, —PO—R$^b$R$^b$, or —O—PO (OR$^b$)$_2$, in which each R$^b$ independently has the meaning given above.

Preferred groups which may replace a hydroxyl group include a halogen atom or an amino, mercapto, azide, alkyl, hydroxyalkyl, hydroxyalkenyl, hydroxyalkynyl or alkylsilyloxy group. Also preferred are cyclodextrins in which a hydroxy group has been esterified to form a sulfate or phosphate ester. Numerous derivatised cyclodextrins are available commercially, and any of these may be used in the present invention. For example the following derivatives of α-cyclodextrin are commercially available (some in the form of a salt): hexakis butyldimethylsilyl)-α-cyclodextrin; hexakis (6-azido-6-deoxy)-α-cyclodextrin; hexakis (6-amino-6-deoxy)-α-cyclodextrin; hexakis (6-bromo-6-deoxy)-α-cyclodextrin; hexakis (6-iodo-6-deoxy)-α-cyclodextrin; hexakis (6-mercapto-6-deoxy)-α-cyclodextrin; carboxymethyl-α-cyclodextrin; α-cyclodextrin phosphate; α-cyclodextrin sulfate; (2-hydroxypropyl)-α-cyclodextrin; hexakis (3-amino-3-deoxy)-α-cyclodextrin; and methyl-α-cyclodextrin.

The following derivatives of β-cyclodextrin are commercially available: heptakis (6-O-t-butyldimethylsilyl)-β-cyclodextrin; heptakis (6-azido-6-deoxy)-β-cyclodextrin; heptakis (6-amino-6-deoxy)-β-cyclodextrin; heptakis (6-bromo-6-deoxy)-β-cyclodextrin; heptakis (6-deoxy-6-iodo)-β-cyclodextrin; 6-monotosyl-β-cyclodextrin; 6-monodeoxy-6-monoamino-β-cyclodextrin; heptakis (6-deoxy-6-mercapto)-β-cyclodextrin; carboxymethyl-β-cyclodextrin; β-cyclodextrin phosphate; β-cyclodextrin sulfate; (2-hydroxypropyl)-β-cyclodextrin; heptakis (3-amino-3-deoxy)-β-cyclodextrin; A,D-6-diamino-6-dideoxy-β-cyclodextrin; and methyl-β-cyclodextrin.

The following derivatives of γ-cyclodextrin are commercially available: octakis (6-O-t-butyldimethylsilyl)-γ-cyclodextrin; octakis (6-azido-6-deoxy)-γ-cyclodextrin; octakis (6-amino-6-deoxy)-γ-cyclodextrin; octakis (6-bromo-6-deoxy)-γ-cyclodextrin; octakis (6-deoxy-6-iodo)-γ-cyclodextrin; and octakis (6-deoxy-6-mercapto)-γ-cyclodextrin; carboxymethyl-γ-cyclodextrin; γ-cyclodextrin phosphate; γ-cyclodextrin sulfate; (2-hydroxypropyl)-γ-cyclodextrin; octakis (3-amino-3-deoxy)-γ-cyclodextrin; and methyl-γ-cyclodextrin.

Any of these may be incorporated into a conjugate or reagent of the present invention.

In preferred embodiments of the invention, either the 3-hydroxy group or the 6-hydroxy group, or both, present in one glucose ring is replaced by an $NH_2$ group. This provides a convenient method of covalently bonding the cyclodextrin to the linker of the conjugate or reagent according to the invention, as described below. Alternative groups which may substitute for the 3- and/or 6-hydroxy group to provide convenient synthesis routes include thiol, azido, —O-propargyl, aldehyde and carboxy groups.

The cyclodextrin may be bonded to the rest of the linker from any suitable position in one or more cyclic glucose groups. In one preferred embodiment, the cyclodextrin is bonded to the rest of the linker via the 3- or the 6-position. Other positions may also provide bonding sites, either via hydroxy groups, or via substituents as described above.

The Payload

The conjugates and reagents of the invention carry a payload which is a therapeutic, diagnostic or labelling agent. This payload is covalently bonded to the cyclodextrin and to the protein or peptide via a linker. A single molecule of a therapeutic, diagnostic or labelling agent may be present, or two or more molecules may be present. The inclusion of one or more drug molecules, for example a cytotoxic agent or a toxin, is preferred. Auristatins, maytansinoids and duocarmycins are typical cytotoxic drugs. It is often preferred that drug conjugates, particularly antibody drug conjugates, should contain multiple copies of the drug. Labelling agents (which should be understood to include imaging agents) may for example include a radionuclide, a fluorescent agent (for example an amine derivatised fluorescent probe such as 5-dimethylaminonaphthalene-1-(N-(2-aminoethyl))sulfonamide-dansyl ethylenediamine, Oregon Green® 488 cadaverine (catalogue number O-10465, Molecular Probes), dansyl cadaverine, N-(2-aminoethyl)-4-amino-3,6-disulfo-1,8-naphthalimide, dipotassium salt (lucifer yellow ethylenediamine), or rhodamine B ethylenediamine (catalogue number L 2424, Molecular Probes), or a thiol derivatised fluorescent probe for example BODIPY® FL L-cystine (catalogue number B-20340, Molecular Probes). Biotin may also be used.

Preferably the payload is a therapeutic agent, especially one of those mentioned above.

It is known that therapeutic, diagnostic or imaging agents may form complexes with cyclodextrins, where said agent is complexed by the cyclodextrin via non-covalent bonding. The conjugates according to the present invention may contain a second therapeutic, diagnostic or imaging agent, particularly a second therapeutic agent, in addition to that required as an essential feature of a conjugate according to the invention, said second agent being present in the form of a complex with the cyclodextrin.

The Protein

For convenience in this section and elsewhere, "protein" should be understood to include "protein and peptide" except where the context requires otherwise.

Suitable proteins which may be present in the conjugates of the invention include for example peptides, polypeptides, antibodies, antibody fragments, enzymes, cytokines, chemokines, receptors, blood factors, peptide hormones, toxin, transcription proteins, or multimeric proteins.

Enzymes include carbohydrate-specific enzymes, proteolytic enzymes and the like, for example the oxidoreductases, transferases, hydrolases, lyases, isomerases and ligases disclosed by U.S. Pat. No. 4,179,337. Specific enzymes of interest include asparaginase, arginase, adenosine deaminase, superoxide dismutase, catalase, chymotrypsin, lipase, uricase, bilirubin oxidase, glucose oxidase, glucuronidase, galactosidase, glucocerbrosidase, and glutaminase.

Blood proteins include albumin, transferrin, Factor VII, Factor VIII or Factor IX, von Willebrand factor, insulin, ACTH, glucagen, somatostatin, somatotropins, thymosin, parathyroid hormone, pigmentary hormones, somatomedins, erythropoietin, luteinizing hormone, hypothalamic releasing factors, antidiuretic hormones, prolactin, interleukins, interferons, for example IFN-α or IFN-β, colony stimulating factors, haemoglobin, cytokines, antibodies, antibody fragments, chorionicgonadotropin, follicle-stimulating hormone, thyroid stimulating hormone and tissue plasminogen activator.

Other proteins of interest are allergen proteins disclosed by Dreborg et al Crit. Rev. Therap. Drug Carrier Syst. (1990) 6 315-365 as having reduced allergenicity when conjugated with a polymer such as poly(alkylene oxide) and consequently are suitable for use as tolerance inducers. Among the allergens disclosed are Ragweed antigen E, honeybee venom, mite allergen and the like.

Glycopolypeptides such as immunoglobulins, ovalbumin, lipase, glucocerebrosidase, lectins, tissue plasminogen activator and glycosylated interleukins, interferons and colony stimulating factors are of interest, as are immunoglobulins such as IgG, IgE, IgM, IgA, IgD and fragments thereof.

Of particular interest are receptor and ligand binding proteins and antibodies and antibody fragments which are used in clinical medicine for diagnostic and therapeutic purposes.

Antibody-drug conjugates, especially where the drug is a cytotoxic drug, for example an auristatin, a maytansinoid or a duocarmycin, are an especially preferred embodiment of the invention. Except where the context requires otherwise, any reference in this Specification to a conjugate of the invention should be understood to include a specific reference to an antibody drug conjugate.

The protein may be derivatised or functionalised if desired. In particular, prior to conjugation, the protein, for example a native protein, may have been reacted with various blocking groups to protect sensitive groups thereon; or it may have been previously conjugated with one or more polymers or other molecules. It may contain a polyhistidine tag, which during the conjugation reaction can be targeted by the conjugating reagent.

Bonding of the Protein or Peptide, and Conjugating Reagents

The conjugating reagents of the invention are of the general type disclosed in WO 2005/007197 and WO 2010/100430. The functional groupings II and II' are chemical equivalents of each other. When a reagent containing a group II reacts with a protein, a first leaving group L is lost to form in situ a conjugating reagent containing a group II' which reacts with a first nucleophile. The second leaving group L is then lost, and reaction with a second nucleophile occurs. Thus as an alternative to using a reagent containing the functional grouping II as starting material, reagents containing the functional grouping II' may be used as starting material.

A leaving group L may for example be —SP, —OP, —SO$_2$P, —OSO$_2$P, —N$^+$PR$^2$R$^3$, halogen, or —OØ, in which P represents a hydrogen atom or an alkyl (preferably C$_{1-6}$ alkyl), aryl (preferably phenyl), or alkyl-aryl (preferably C$_{1-6}$alkyl-phenyl) group, or is a group which includes a portion —(CH$_2$CH$_2$O)$_n$— in which n is a number of two or more, and each of R$^2$ and R$^3$ independently represents a hydrogen atom, a C$_{1-4}$alkyl group, or a group P, and Ø represents a substituted aryl, especially phenyl, group, containing at least one substituent, for example —CN, —NO$_2$, —CF$_3$, —CO$_2$R$^a$, —COH, —CH$_2$OH, —COR$^a$, —OR$^a$, —OCOR$^a$, —OCO$_2$R$^a$, —SR$^a$, —SOR$^a$, —SO$_2$R$^a$, —NR$^a$COR$^a$, —NR$^a$CO$_2$R$^a$, —NO, —NHOH, —NR$^a$ OH, —CH=N—NR$^a$ COR$^a$, —N$^+$R$^a_3$, halogen, especially chlorine or, especially, fluorine, —CCRE, and —CH=CRE$_2$, in which each R$^a$ represents a hydrogen atom or an alkyl (preferably C$_{1-6}$alkyl), aryl (preferably phenyl), or alkyl-aryl (preferably C$_{1-6}$alkyl-phenyl) group. The presence of electron withdrawing substituents is preferred.

Conjugating reagents in which P represents a group which includes a portion —(CH$_2$CH$_2$O)$_n$— in which n is a number of two or more are the subject of our copending application GB 1418186, from which WO 2016/059377 claims priority. This application discloses the following:

"The leaving group may for example include —(CH$_2$CH$_2$O)$_n$—R$^1$ where R$^1$ is a capping group. A very wide range of capping groups may be used. R$^1$ may for example be a hydrogen atom, an alkyl group, especially a C$_{1-4}$alkyl group, particularly a methyl group, or an optionally substituted aryl group, for example an optionally substituted phenyl group, for example a tolyl group. Alternatively, the capping group may include a functional group such as a carboxyl group or an amine group. Such capping groups may for example have the formula —CH$_2$CH$_2$CO$_2$H or —CH$_2$CH$_2$NH$_2$, and may be prepared by functionalising the terminal unit of a —(CH$_2$CH$_2$O)$_n$— chain. Alternatively, rather than being terminated by a capping group, the —(CH$_2$CH$_2$O)$_n$— group may have two points of attachment within the conjugating reagent such that chemically the equivalent of two leaving groups are present, capable of reacting with two nucleophiles.

The —(CH$_2$CH$_2$O)$_n$— portion of the leaving group is based on PEG, polyethylene glycol. The PEG may be straight-chain or branched, and it may be derivatised or functionalised in any way. n is a number of 2 or more, for example 2, 3, 4, 5, 6, 7, 8, 9 or 10. For example, n may be from 5 to 9. Alternatively, n may be a number of 10 or more. There is no particular upper limit for n. n may for example be 150 or less, for example 120 or less, for example 100 or less. For example n may be from 2 to 150, for example from 7 to 150, for example from 7 to 120. The PEG portion —(CH$_2$CH$_2$O)$_n$— of a leaving group may for example have a molecular weight of from 1 to 5 kDa; it may for example be 1 kDa, 2 kDa, 3 kDa, 4 kDa or 5 kDa. A leaving group may if desired contain two or more portions —(CH$_2$CH$_2$O)$_n$— separated by one or more spacers.

A leaving group in a conjugating reagent according to the invention is suitably of the formula —SP, —OP, —SO$_2$P, —OSO$_2$P, —N$^+$R$^2$R$^3$, in which P is a group which includes a portion —(CH$_2$CH$_2$O)$_n$— and each of R$^2$ and R$^3$ independently represents a hydrogen atom, a C$_{1-4}$alkyl group, or a group P. Preferably each of R$^2$ and R$^3$ represents a C$_{1-4}$alkyl group, especially a methyl group, or, especially, a hydrogen atom. Alternatively, the conjugating reagent may include a group of formula —S—P—S—; —O-β-O—; —SO$_2$-β-SO$_2$—; —OSO$_2$-β-OSO$_2$—; and —N$^+$R$^2$R$^3$—P—N$^+$R$^2$R$^3$—. Specific groups of this type include —S—(CH$_2$CH$_2$O)$_n$—S—, —O—(CH$_2$CH$_2$O)$_n$—O—; —SO$_2$—(CH$_2$CH$_2$O)$_n$—SO$_2$—; —OSO$_2$—(CH$_2$CH$_2$O)$_n$—OSO$_2$—; or —N$^+$R$^2$R$^3$—(CH$_2$CH$_2$O)$_n$—N$^+$R$^2$R$^3$—. They can also include groups of the type:

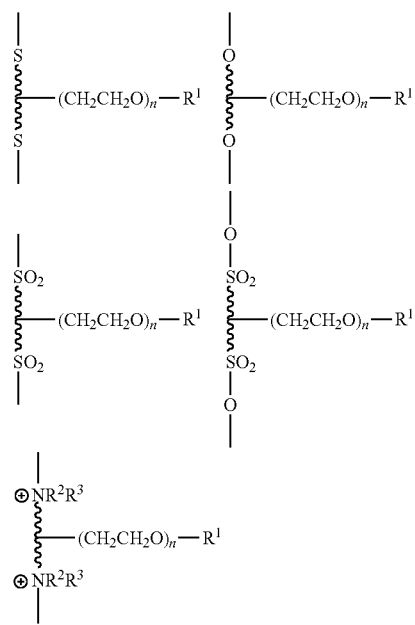

where the —(CH$_2$CH$_2$O)$_n$— group is carried by any suitable linking group, for example an alkyl group. These divalent groups are chemically equivalent to two leaving groups capable of reacting with two nucleophiles."

An especially preferred leaving group L present in a novel conjugating reagent according to the present invention is —SP or —SO$_2$P, especially —SO$_2$P. Within this group, one preferred embodiment is where P represents a phenyl or, especially, a tosyl group. Another preferred embodiment is where P represents a group which includes a portion —(CH$_2$CH$_2$O)$_n$—, especially one in which n has one of the values mentioned above, especially 7. An especially preferred leaving group L is —SO$_2$—(CH$_2$CH$_2$O)$_n$—H/Me, especially —SO$_2$—(CH$_2$CH$_2$O)$_7$—H/Me. Throughout this Specification, any reference to a leaving group L should be understood to include a specific reference to these preferred groups, especially —SO$_2$—(CH$_2$CH$_2$O)$_n$—H/Me, and more especially —SO$_2$—(CH$_2$CH$_2$O)$_7$—H/Me.

The electron withdrawing group W may for example be a keto group —CO—, an ester group —O—CO— or a sulfone group —SO$_2$—. Preferably W' represents one of these groups or a group obtainable by reduction of one of these groups as described below. Preferably W represents a keto group, and preferably W' represents a keto group or a group obtainable by reduction of a keto group, especially a CH.OH group.

Preferably the groupings F' and F have the formula:

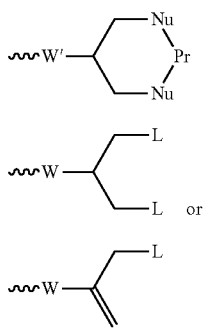

(Ia)

(IIa)

(II'a)

especially

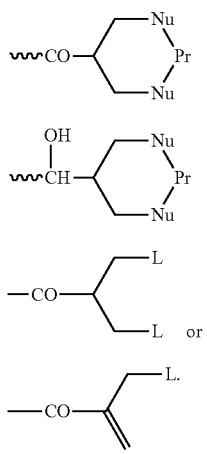

(Ib)

(Ic)

(IIb)

(II'b)

Nucleophilic groups in proteins are for example provided by cysteine, lysine or histidine residues, and Nu may for example be a sulfur atom or an amine group. In one preferred embodiment of the invention, each Nu represents a sulfur atom present in a cysteine residue present in the protein. Such structures may be obtained by reduction of a disulfide bond present in the protein. In another embodiment, each Nu represents an imidazole group present in a histidine residue present in a polyhistidine tag attached to said protein.

The Linker

The linker which connects the therapeutic, diagnostic or labelling agent to the protein or peptide bonding portion in the conjugates of the invention or to the functional grouping in conjugating reagents of the invention must include one or more cyclodextrins as described above. It may also contain any other desired groups, particularly any of the conventional groups commonly found in this field.

Subsection (i). In one embodiment, the linker between the payload and the grouping of formula F'/F, and particularly that portion of the linker immediately adjacent the grouping of formula F'/F, may include an alkylene group (preferably a $C_{1-10}$ alkylene group), or an optionally-substituted aryl or heteroaryl group, any of which may be terminated or interrupted by one or more oxygen atoms, sulfur atoms, $—NR^a$ groups (in which $R^a$ represents a hydrogen atom or an alkyl (preferably $C_{h6}$ alkyl), aryl (preferably phenyl), or alkyl-aryl (preferably $C_{1-6}$ alkyl-phenyl) group), keto groups, $—O—CO—$ groups, $—CO—O—$ groups, $—O—CO—O$, $—NR—CO—O—$, $—CO—NR^a—$ and/or $—NR^a.CO—$ groups. Suitable aryl groups include phenyl and naphthyl groups, while suitable heteroaryl groups include pyridine, pyrrole, furan, pyran, imidazole, pyrazole, oxazole, pyridazine, pyrimidine and purine. Especially preferred as that portion of the linker immediately adjacent the group F/F' are aryl or heteroaryl groups, especially phenyl groups.

The aryl or heteroaryl group may be adjacent a further portion of the linking group which is, or contains, a $—NR^a.CO—$ or $—CO.NR^a—$ group, for example an $—NH.CO—$ or $—CO.NH—$ group. Here and elsewhere throughout this Specification, where a group $R^a$ is present, this is preferably a $C_{1-4}$ alkyl, especially a methyl group or, especially, a hydrogen atom.

Substituents which may be present on an optionally substituted aryl, especially phenyl, or heteroaryl group include for example one or more of the same or different substituents selected from alkyl (preferably $C_{1-4}$ alkyl, especially methyl, optionally substituted by OH or $CO_2H$), $—CN$, $—CF_3$, $—NO_2$, $—NR^a_2$, $—CO_2R^a$, $—COH$, $—CH_2OH$, $—COR^a$, $—OCOR^a$, $—OCO_2R^a$, $—SOR^a$, $—SO_2R^a$, $—NR^aCOR^a$, $—NR^a.CO_2R^a$, $—NO$, $—NR^a.OH$, $—CH=N—NR^a.COR^a$, $—N^+R^a_3$, halogen, for example fluorine or chlorine, $—C≡CR^a$, and $—C=CR^a_2$, in which each $R^a$ independently represents a hydrogen atom or an alkyl (preferably $C_{1-6}$ alkyl), aryl (preferably phenyl), or alkyl-aryl (preferably $C_{1-6}$alkyl-phenyl) group. The presence of electron withdrawing substituents is especially preferred. Preferred substituents include for example $—CN$, $—NO_2$, $—OR^a$, $—NR^a.COR^a$, $—NHOH$ and $—NR^a.CO_2R^a$, especially CN and $NO_2$.

Preferably the linker includes one of the above groups adjacent the grouping F'/F. Especially preferred are conjugates and conjugating reagents which include the grouping:

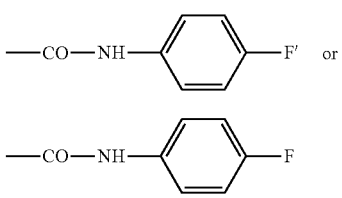

III

IV or, especially:

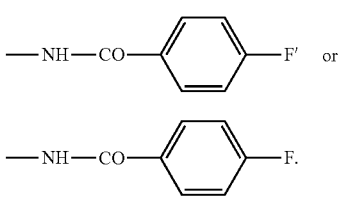

V

VI

Any of the above structures may be adjacent to any of the structures mentioned in subsections (ii) and (iii) below.

In all the above formulae III, IV, V and VI, preferably F' has the formula I, for example Ia or Ib above, and preferably F has the formula II or II', for example IIa, IIb, II'a or II'b above.

Subsection (ii). In one embodiment, the linker may contain a degradable group, i.e. it may contain a group which breaks under physiological conditions, separating the payload from the protein to which it is, or will be, bonded. Alternatively, it may be a linker that is not cleavable under physiological conditions. Where a linker breaks under physiological conditions, it is preferably cleavable under intracellular conditions. Where the target is intracellular, preferably the linker is substantially insensitive to extracellular conditions (i.e. so that delivery to the intracellular target of a sufficient dose of the therapeutic agent is not prohibited).

Where the linker contains a degradable group, this is generally sensitive to hydrolytic conditions, for example it may be a group which degrades at certain pH values (e.g. acidic conditions). Hydrolytic/acidic conditions may for example be found in endosomes or lysosomes. Examples of groups susceptible to hydrolysis under acidic conditions include hydrazones, semicarbazones, thiosemicarbazones, cis-aconitic amides, orthoesters and ketals. Examples of groups susceptible to hydrolytic conditions include:

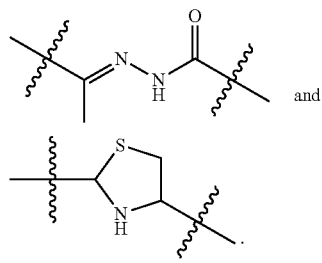

In a preferred embodiment, the linker includes

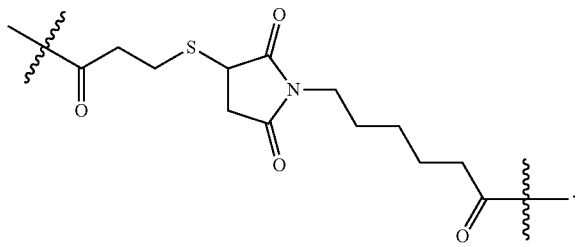 [SMILES: *C(=O)CCCCCN1C(=O)CC(SCCC(*)=O)C1=O]

For example, it may include:

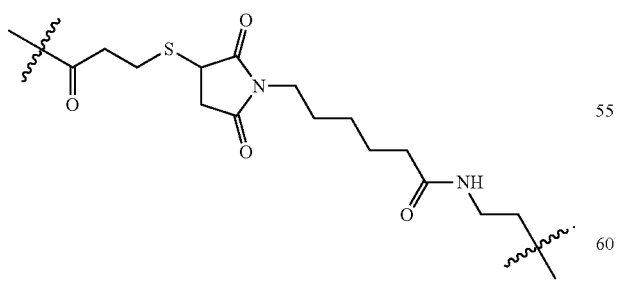

The linker may also be susceptible to degradation under reducing conditions. For example, it may contain a disulfide group that is cleavable on exposure to biological reducing agents, such as thiols. Examples of disulfide groups include:

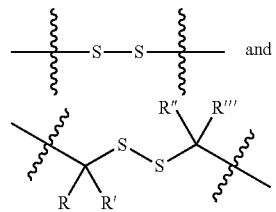

in which R, R', R" and R'" are each independently hydrogen or $C_{1-4}$alkyl. In a preferred embodiment the linker includes

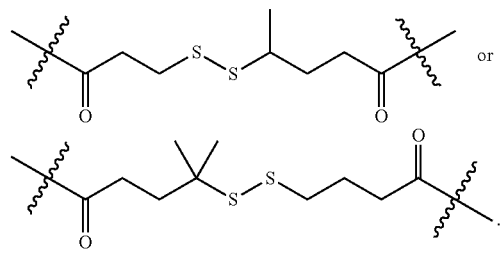

For example, it may include

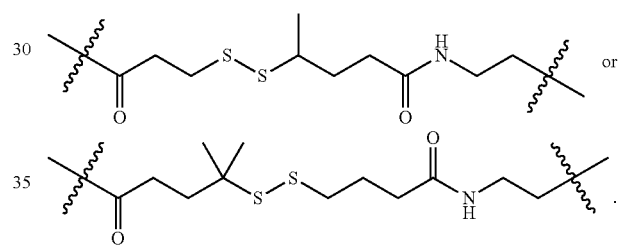

The linker may also contain a group which is susceptible to enzymatic degradation, for example it may be susceptible to cleavage by a protease (e.g. a lysosomal or endosomal protease) or peptidase. In an especially preferred embodiment of the invention, a portion of the linker contains a peptidyl group comprising at least one, for example at least two, at least three, at least four or at least five amino acid residues, specifically naturally-occurring alpha amino acids. For example, that portion of the linker may contain the sequence Phe-Leu, Gly-Phe-Leu-Gly, Val-Ala, Val-Cit, Phe-Lys, or Glu-Glu-Glu, and presence of a Val-Cit peptidyl group is preferred. Linkers containing the sequence Val-Cit-PAB, as discussed below, are especially preferred.

A particularly preferred example of a group susceptible to enzymatic degradation is:

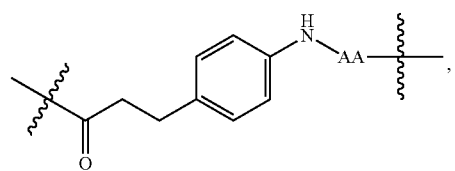

wherein AA represents an amino acid sequence, especially a protease-specific amino acid sequence, such as one of those mentioned above, especially Val-Cit.

In a preferred embodiment, the linker includes:

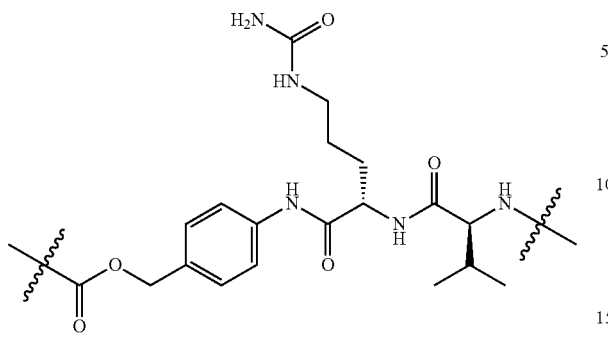

For example, it may include

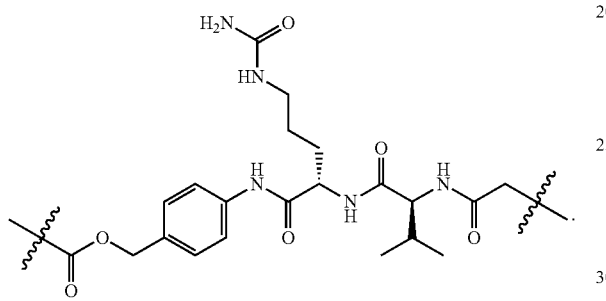

The linker may carry a single payload D, or more than one group D. Multiple groups D may be incorporated by the use of a branching linker, which may for example incorporate an aspartate or glutamate or similar residue. This introduces a branching element of formula:

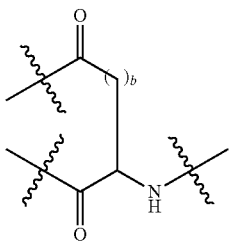

where b is 1, 2, 3 or 4, b=1 being aspartate and b=2 being glutamate, and b=3 representing one preferred embodiment. Each of the acyl moieties in the above formula may be coupled to a group D. The branching group above may incorporate a —CO.CH$_2$— group, thus:

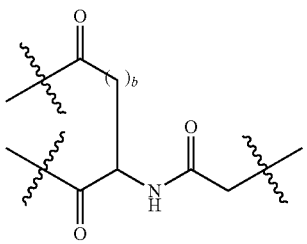

If desired, the aspartate or glutamate or similar residue may be coupled to further aspartate and/or glutamate and/or similar residues, for example:

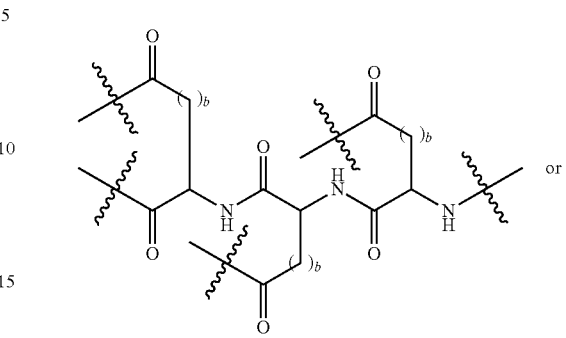

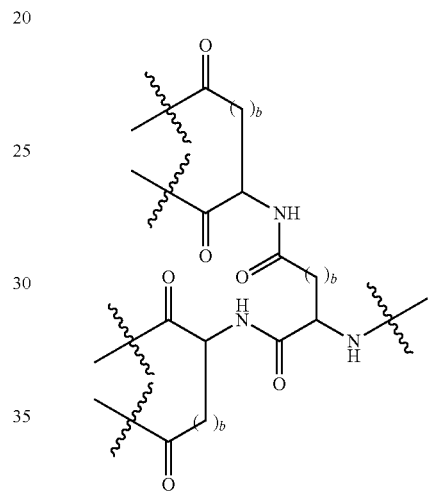

and so on.

In a similar way, the amino acids lysine, serine, threonine, cysteine, arginine or tyrosine or similar residues may be introduced to form a branching group, thus:

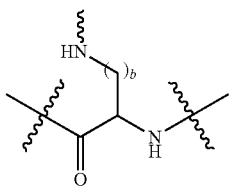

in which b is 4 for lysine, and

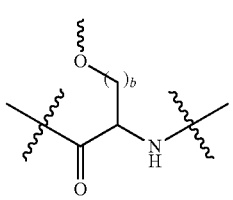

in which b is 1 for serine.

Similar branching groups may be used to incorporate the cyclodextrin group into the linker, and such structures form a further preferred embodiment of the invention. So, for example, one of the branching elements mentioned above, for example an aspartate, glutamate, lysine or serine or similar residue may be present with one branch leading to a therapeutic, diagnostic or labelling agent, for example a drug D, while the other leads to a branch containing the cyclodextrin group. The various linker portions mentioned above may be present at any location either before or after a branching group.

As will be apparent, many alternative configurations for the linker between the grouping F/F' and the payload are possible. One preferred configuration may be represented schematically as follows:

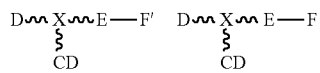

in which E represents one of the groups mentioned in subsection (i) above, and X represents one of the groups mentioned in this subsection (ii).

A specific, particularly preferred construction is shown below:

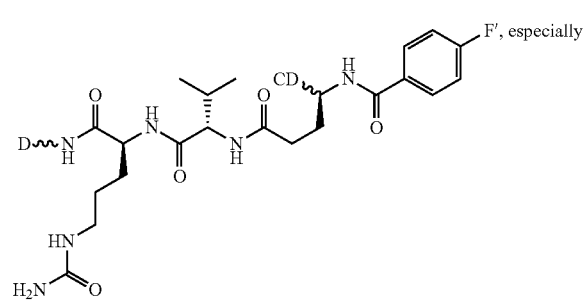

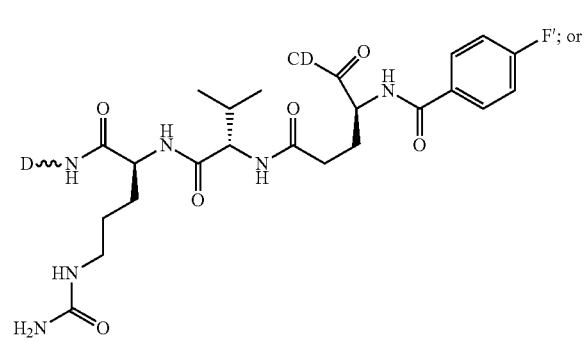

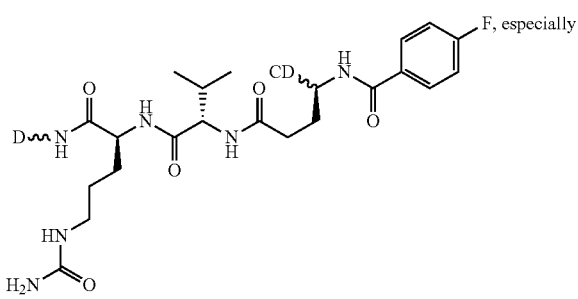

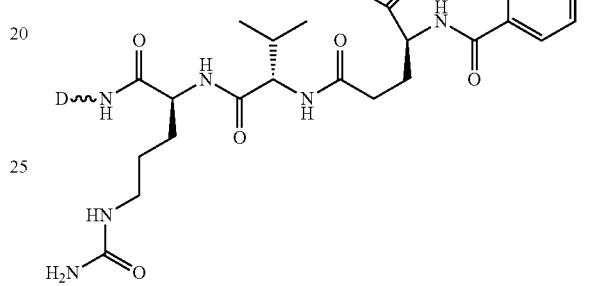

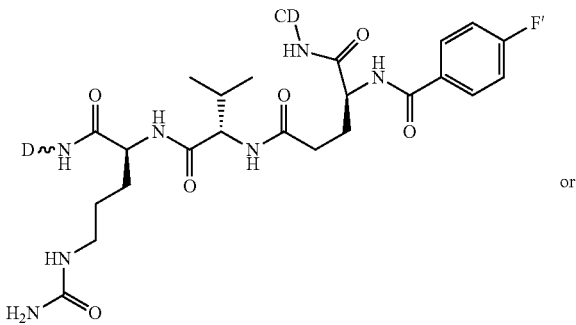

in which D, CD, F' and F have the meanings given above. Conveniently, the cyclodextrin may be bonded to the rest of the linker in the above formulae via an amide bond, thus:

Particularly preferred examples of such structures are as follows:

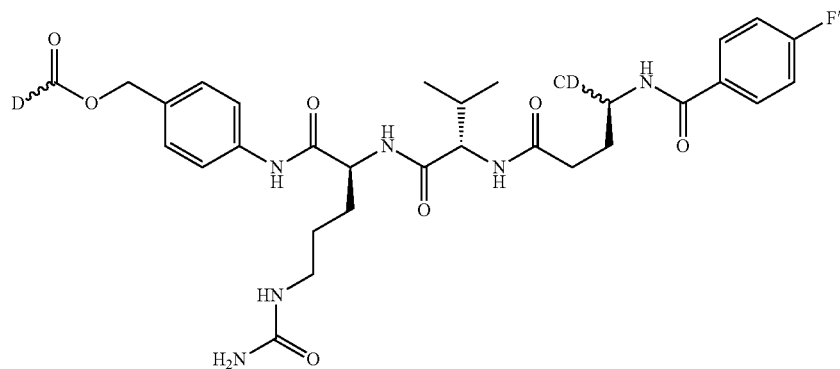
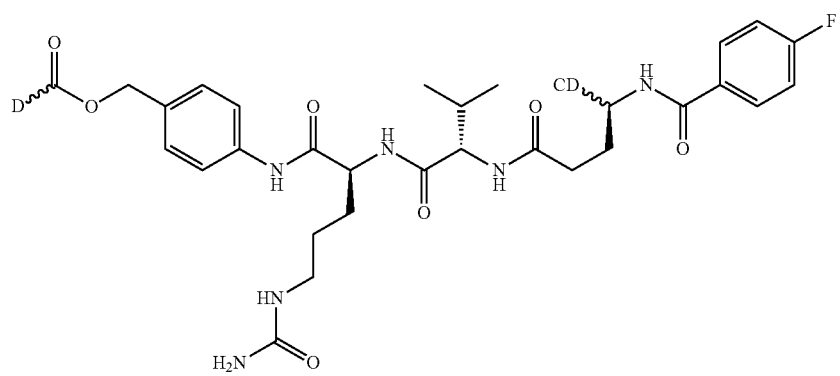
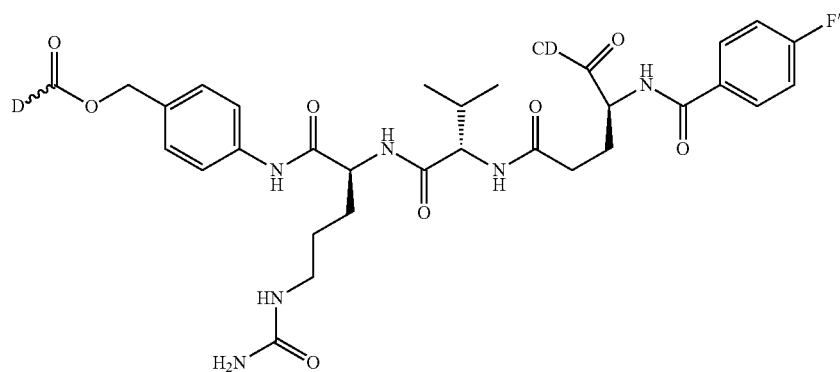
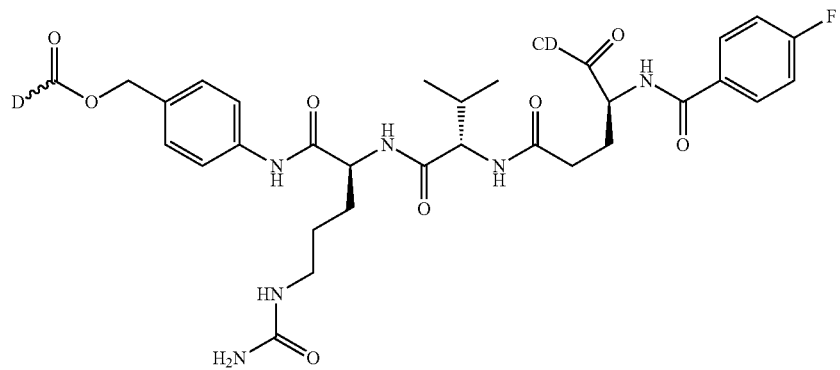

-continued

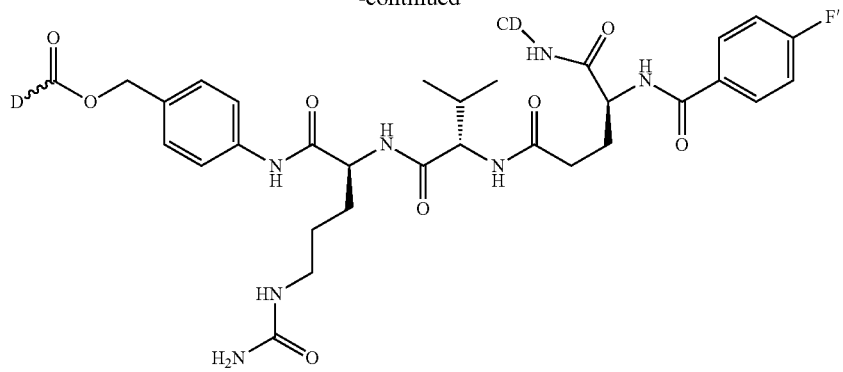

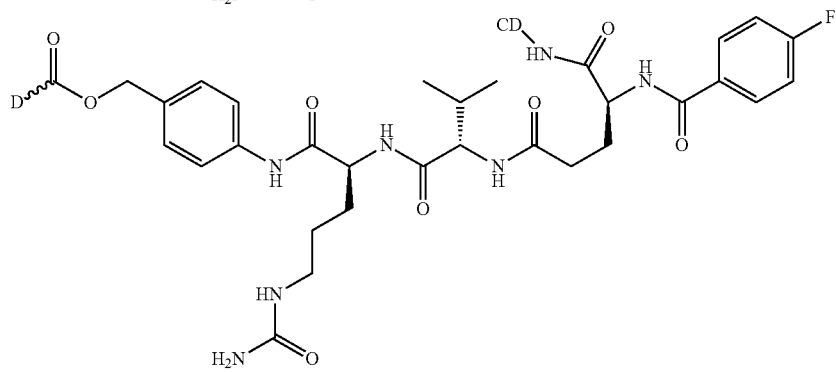

Such conjugates and reagents may be prepared from a cyclodextrin in which the 3- or 6-hydroxy group has been replaced by an $NH_2$ group, as described above.

Subsection (iii). The linker which connects the therapeutic, diagnostic or labelling agent to the protein or peptide in the conjugates of the invention or to the functional grouping in the conjugating reagents of the invention may if desired contain PEG, or it may be free from PEG. It may for example contain PEG in the backbone of the linker, shown schematically thus:

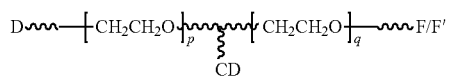

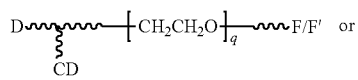

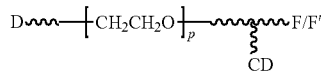

Alternatively or additionally, PEG may be present as a pendant chain on the linker, shown schematically as:

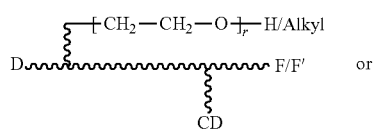

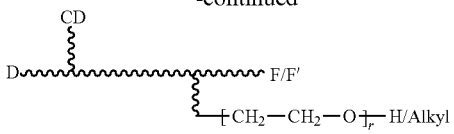

In these formulae, p, q and r represent the number of ethylene glycol units present in the various possible PEG chains present in the linker of the conjugate or the reagent. For clarity, the PEG units are shown as straight-chain units, but it will be understood that any of the units may include branched chains.

If PEG is present, the total number of —$CH_2$—$CH_2$—O—)— units present in the conjugates and reagents of the invention will of course depend on the intended application. For some applications, high molecular weight PEGs may be used, for example the number average molecular weight may be up to around 75,000, for example up to 50,000, 40,000 or 30,000 g/mole. For example, the number average molecular weight may be in the range of from 500 g/mole to around 75,000. However, smaller PEG portions may be preferred for some applications. For example a PEG portion may have a molecular weight up to 3,000 g/mole. However, PEG groups containing as few as 2 ethylene glycol repeat units, for example from 2 to 50 repeat units, are useful for some applications. PEG-containing portions with 2, 3, 4, 5, 6, 7, 8, 9 or 10 repeat units, or 12, 20, 24, 36, 40 or 48 repeat units, may for example be used.

Subsection (iv). The linker which connects the therapeutic, diagnostic or labelling agent to the protein or peptide in the conjugates of the invention or to the functional grouping in the conjugating reagents of the invention may contain two or more cyclodextrins, and these may be present in the backbone of the linker or as pendant groups tethered to the backbone of the linker. This may be illustrated schematically for two pendant cyclodextrins thus:

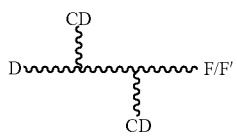

and obviously more than two such groups may similarly be present.

Multiple cyclodextrins may be incorporated into the linker using any suitable method. A polypeptide chain may for example be introduced by reaction with any reactive grouping present in any of the linker portions discussed above. Branching groups of the formulae described above may be used. For example, in one specific embodiment, two cyclodextrins may be incorporated by use of a structure:

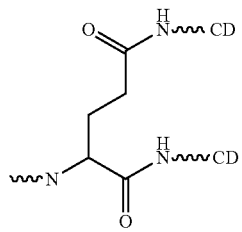

Alternatively, branching may be introduced by use of a polyol functionality, for example:

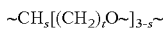

in which s is 0, 1 or 2, and t is 1 to 4. For example, in one specific embodiment, three pendant polypeptide chains may be incorporated by use of a structure:

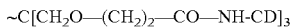

Conjugating Processes

Conjugating reagents according to the invention may be reacted with a protein or peptide to form a conjugate according to the invention, and such a reaction forms a further aspect of the invention. Thus, a conjugating reagent including the functional grouping II or II' is reacted with a protein or peptide to form a conjugate including the grouping I. The immediate product of the conjugation process is a conjugate which contains an electron-withdrawing group W. However, the conjugation process is reversible under suitable conditions. This may be desirable for some applications, for example where rapid release of the protein is required, but for other applications, rapid release of the protein may be undesirable. It may therefore be desirable to stabilise the conjugates by reduction of the electron-withdrawing moiety W to give a moiety which prevents release of the protein. Accordingly, the process described above may comprise an additional optional step of reducing the electron withdrawing group W in the conjugate. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminium alkoxide, and lithium aluminium hydride.

Thus, for example, a moiety W containing a keto group may be reduced to a moiety containing a CH(OH) group; an ether group $CH.OR^a$ may be obtained by the reaction of a hydroxy group with an etherifying agent; an ester group $CH.O.C(O)R^a$ may be obtained by the reaction of a hydroxy group with an acylating agent; an amine group $CH.NH_2$, $CH.NHR^a$ or $CH.NR^a{}_2$ may be prepared from a ketone by reductive amination; or an amide $CH.NHC(O)R^a$ or $CH.N(C(O)R^a)_2$ may be formed by acylation of an amine. A sulfone may be reduced to a sulfoxide, sulfide or thiol ether.

A key feature of using conjugating reagents of the invention is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. The leaving moiety serves to mask a latent conjugated double bond that is not exposed until after the first alkylation has occurred to give a reagent including the functional grouping II' and bis-alkylation results from sequential and interactive Michael and retro-Michael reactions. The cross-functional alkylating agents may contain multiple bonds conjugated to the double bond or between the leaving group and the electron withdrawing group.

Where bonding to the protein is via two sulfur atoms derived from a disulfide bond in the protein, the process may be carried out by reducing the disulfide bond following which the reduced product reacts with the reagent according to the invention. The disulfide bond can be reduced, for example, with dithiothreitol, mercaptoethanol, or tris-carboxyethylphosphine using conventional methods.

Conjugation reactions may be carried out under similar conditions to known conjugation processes, including the conditions disclosed in WO 2005/007197, WO 2009/047500, WO 2014/064423 and WO 2014/064424. The process may for example be carried out in a solvent or solvent mixture in which all reactants are soluble. For example, the protein may be allowed to react directly with the polymer conjugating reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 7.5. The optimal reaction conditions will of course depend upon the specific reactants employed.

Reaction temperatures between 3-40° C. are generally suitable when using an aqueous reaction medium. Reactions conducted in organic media (for example THF, ethyl acetate, acetone) are typically conducted at temperatures up to ambient. In one preferred embodiment, the reaction is carried out in aqueous buffer which may contain a proportion of organic solvent, for example up to 20% by volume of organic solvent, typically from 5 to 20% by volume of organic solvent.

The protein can be effectively conjugated using a stoichiometric equivalent or a slight excess of conjugating reagent. However, it is also possible to conduct the conjugation reaction with an excess stoichiometry of conjugating reagent, and this may be desirable for some proteins.

The excess reagent can easily be removed, for example by ion exchange chromatography or HPLC, during subsequent purification of the conjugate.

Of course, it is possible for more than one conjugating reagent to be conjugated to a protein, where the protein contains sufficient suitable attachment points. For example, in a protein which contains two different disulfide bonds, or in a protein which contains one disulfide bond and also carries a polyhistidine tag, it is possible to conjugate two molecules of the reagent per molecule of protein, and such conjugates form part of the present invention.

Pharmaceutical Compositions and Utility

Conjugates according to the invention in which the payload is a therapeutic agent find utility in the treatment of various medical conditions depending on the nature of the payload. Typically the payload will be a cytotoxic agent and the invention finds utility in the treatment of cancer. Accordingly, the invention further provides a conjugate according to the present invention, particularly one in which the payload is a therapeutic agent and specifically a conjugate which is an antibody-drug conjugate, together with a pharmaceutically acceptable carrier, and optionally together with a further active ingredient. The invention further provides the use of such a conjugate in therapy, and finds utility in a method of treatment of a patient which comprises administering a conjugate or a pharmaceutical composition according to the invention to the patient. The invention further provides the use of a conjugate according to the invention in the manufacture of a medicament for the treatment of, for example, cancer.

Figure 1:
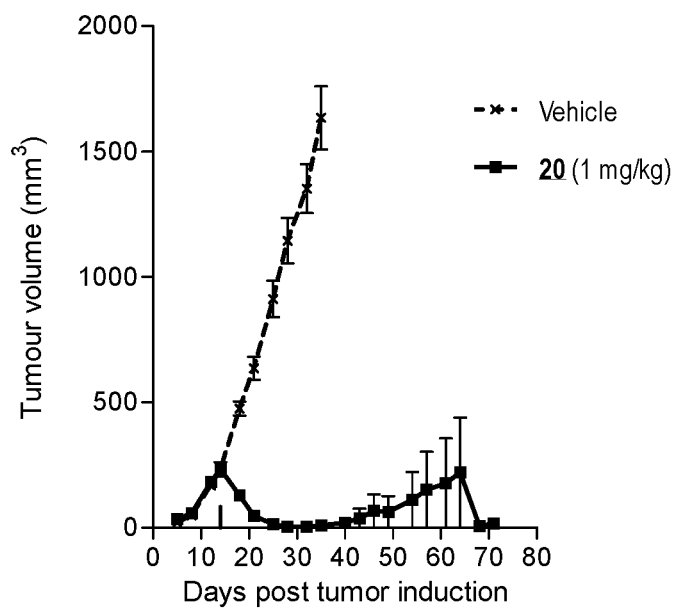
FIGS. 1 to 4 show the results of Example 11.

The following Examples illustrate the invention.

Example 1: Synthesis of Conjugation Reagent 1 Comprising amido-6'β-cyclodextrin and the Auristatin Cytotoxic Payload, MMAE

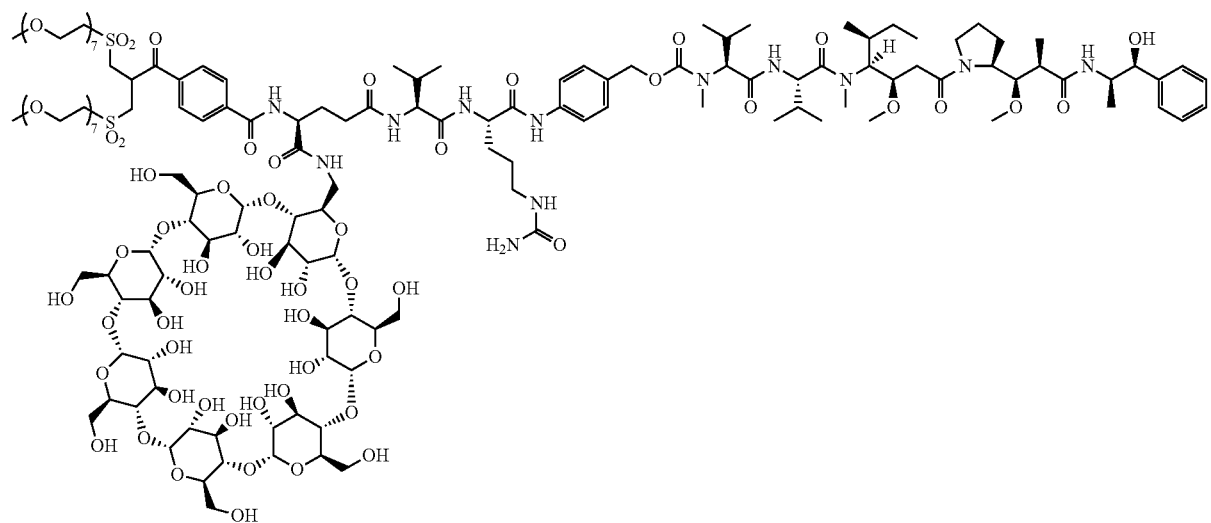

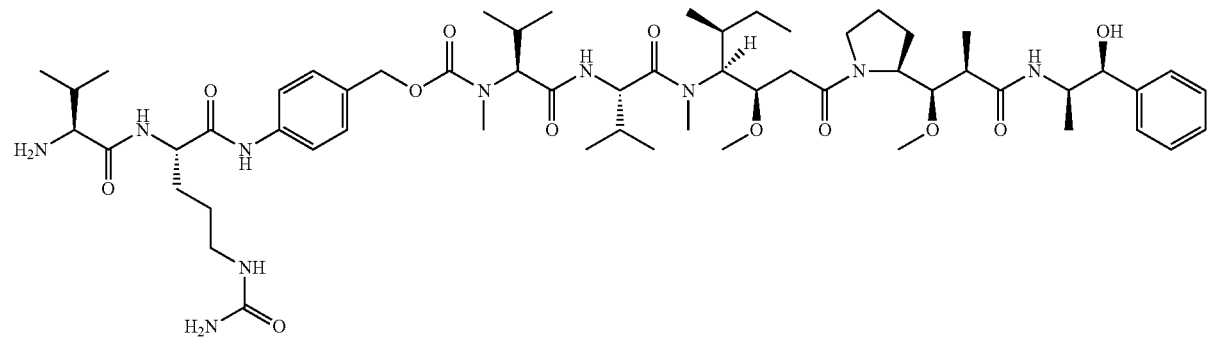

Val-Cit-PAB—MMAE

Step 1: Synthesis of Compound 2.

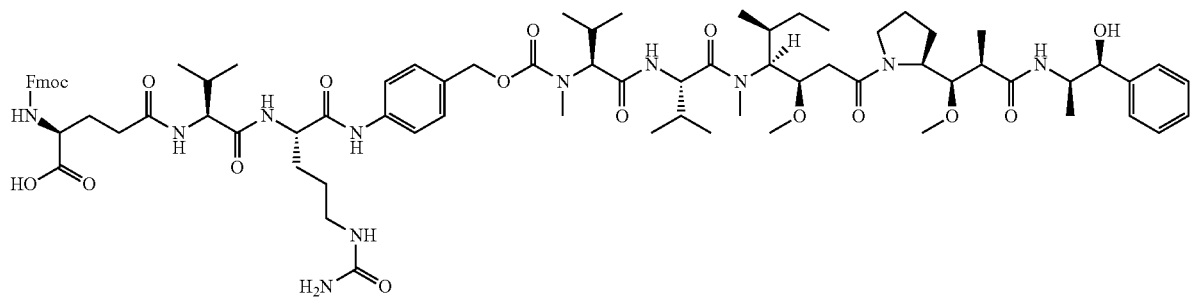

2

To a solution of Fmoc-Glu-(OH)-OAll (48 mg) in DMF (1 mL) was added HATU (110 mg) and the solution was stirred for 30 min at 0° C. To this was added a solution of Val-Cit-PAB-MMAE.TFA salt (Levena Biopharma, 120 mg) and NMM (32 μL) in DMF (1 mL). The reaction mixture was stirred at room temperature for 2.5 h. The solvent was concentrated in vacuo and the crude was dissolved in DMF (1.5 mL) before NMM (32 μL) was added. Tetrakis(triphenylphosphine)palladium(0) (45 mg) was added to the reaction mixture which was then stirred at room temperature for 20 h. The reaction solution was concentrated in vacuo and the residue purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give compound 2 as a white solid (98 mg). m/z [M+H]$^+$ (1475 Da, 100%), [M+2H]$^{2+}$ (738, 50%).

Step 2: Synthesis of Compound 3.

To a solution of compound 2 (23 mg) in DMF (300 μL) was added HATU (7 mg) and the mixture was stirred for 20 min at 0° C. NMM (2 μL) was added to the reaction mixture which was stirred for a further 10 min at room temperature. To a solution of 6-monodeoxy-6-monoamino-β-cyclodextrin hydrochloride (20 mg) in DMF (100 μL) was added NMM (2 μL) and the solution stirred for 15 min at room temperature. The two solutions were then combined and additional quantities of HATU (7 mg) and NMM (2 μL) were added to the combined solution which was stirred for 2 h at room temperature. Piperidine (16 μL) was then added and the reaction mixture left to stir at room temperature for 0.5 h. The reaction solution was concentrated in vacuo and the residue purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give compound 3 as a white solid (15 mg). m/z [M+H]$^+$ (2369, 15%), [M+2H]$^{2+}$ (1185, 100%).

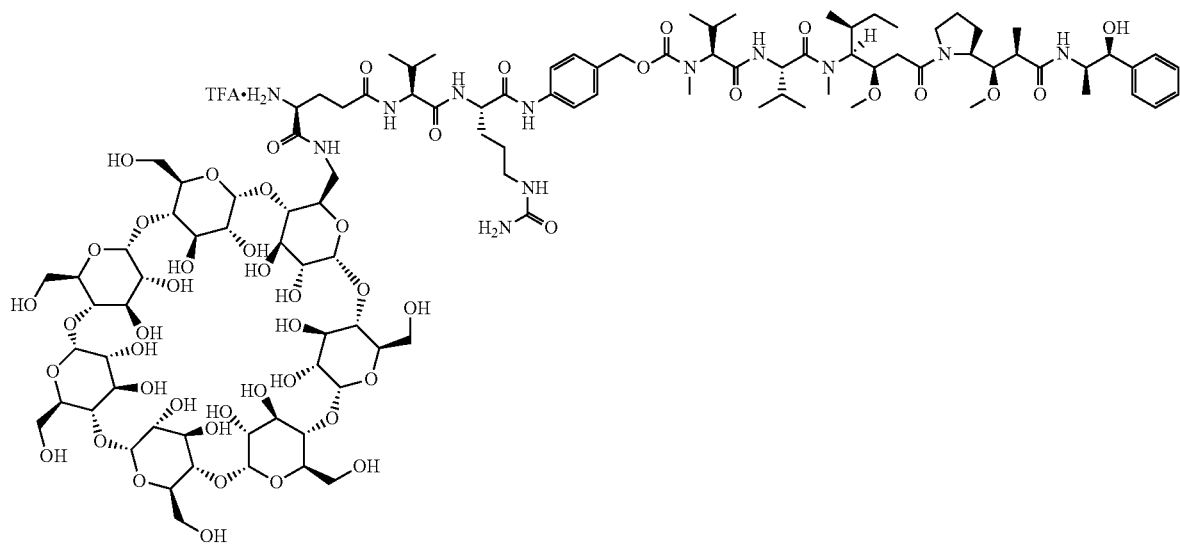

3

Step 3: Synthesis of Compound 4.

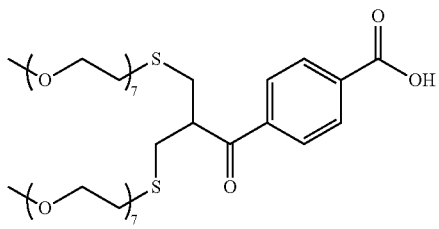

To a stirred solution of 4-[2,2-bis[(p-tolylsulfonyl)-methyl]acetyl]benzoic acid (1.5 g, Nature Protocols, 2006, 1(54), 2241-2252) in DMF (70 mL) was added alpha-methoxy-omega-mercapto hepta(ethylene glycol) (3.2 g) and triethylamine (2.5 mL). The resulting reaction mixture was stirred under an inert nitrogen atmosphere at room temperature. After 19 h, volatiles were removed in vacuo. The resulting residue was dissolved in water (2.4 mL) and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give compound 4 as a thick clear colourless oil (1.8 g). m/z [M+H]$^+$ 901.

Step 4: Synthesis of Reagent 5.

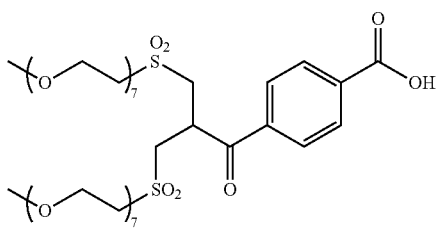

To a stirred solution of 4 (1.32 g) in methanol:water (18 mL, 9:1 v/v) at room temperature was added Oxone® (2.7 g). After 2.5 h, the volatiles were removed in vacuo and water was azeotropically removed with acetonitrile (2×15 mL). The resulting residue was dissolved in dichloromethane (3×10 mL), filtered through a column of magnesium sulfate and washed with dichloromethane (2×7 mL). The eluent and washings were combined and the volatiles were removed in vacuo to give a thick clear pale yellow oil (1.3 g). A portion of the residue (700 mg) was dissolved in water:acetonitrile (1.5 mL, 3:1 v/v), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 5 as a thick clear colourless oil (520 mg). m/z [M+H]$^+$ 965.

Step 5: Synthesis of Reagent 1.

To a solution of reagent 5 (6.3 mg) in DMF (250 µL) was added HATU (2.6 mg) and the solution was stirred at 0° C. for 20 min. NMM (0.5 µL) was added to the solution which was stirred for a further 10 min at room temperature. To a separate solution of compound 3 (15 mg) in DMF (250 µL) was added NMM (0.75 µL) and the solution was stirred for 10 min at 0° C. The two solutions were then combined and additional quantities of HATU (2.6 mg) and NMM (0.75 µL) were added before the reaction mixture was left to stir at room temperature for 2 h. The reaction solution was concentrated in vacuo and the residue purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 1 as a white solid (13 mg). m/z [M+2H]$^{2+}$ (1659, 70%), [M+3H]$^{3+}$ (1106, 100%).

Example 2: Synthesis of Conjugation Reagent 6 Comprising amido-6'-α-cyclodextrin and the Auristatin Cytotoxic Payload, MMAE

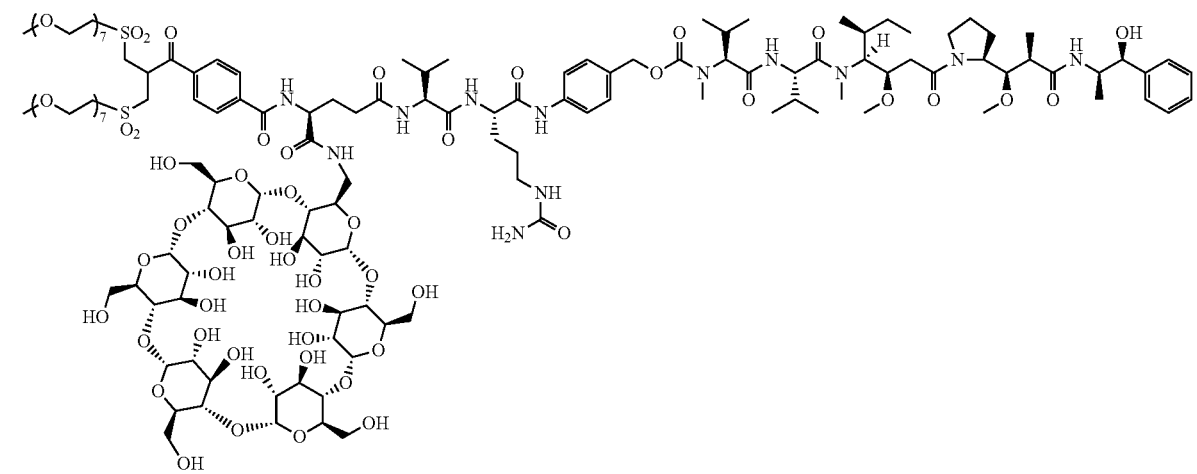

Reagent 6 was synthesised in an analogous way to reagent 1 of Example 1 using 6-monodeoxy-6-monoamino-α-cyclodextrin hydrochloride instead of 6-monodeoxy-6-monoamino-β-cyclodextrin hydrochloride. Reagent 6 was isolated as a white solid. m/z [M+2H]$^{2+}$ (1578, 50%), [M+3H]$^{3+}$ (1052, 100%).

Example 3: Synthesis of Conjugation Reagent 7 Comprising amido-6'-γ-cyclodextrin and the Auristatin Cytotoxic Payload, MMAE

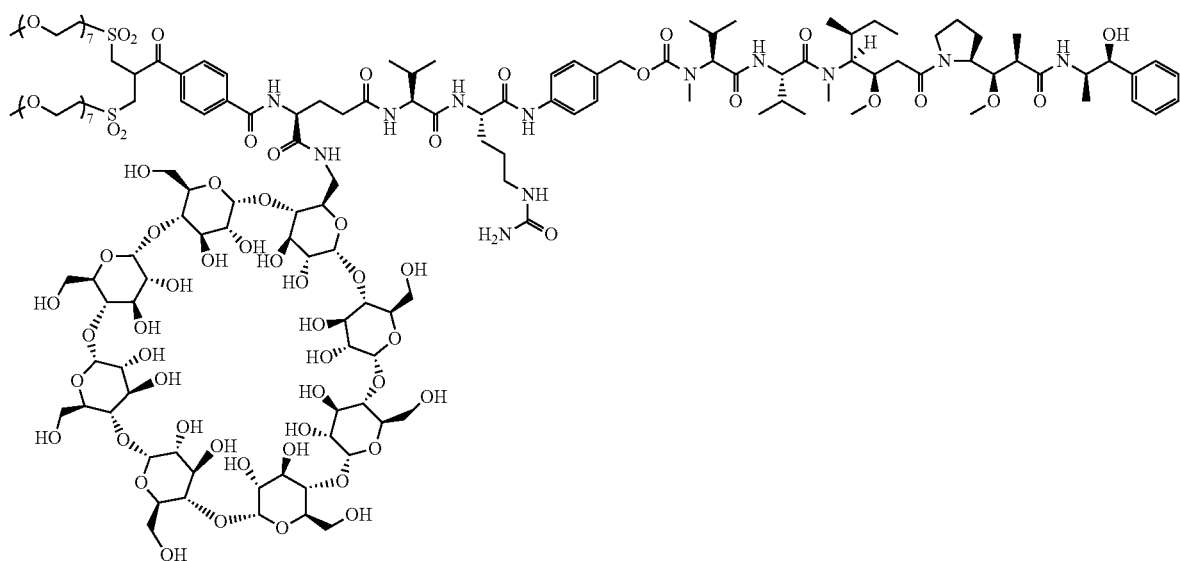

7

Reagent 7 was synthesised in an analogous way to reagent 1 of Example 1 using 6-monodeoxy-6-monoamino-γ-cyclodextrin hydrochloride instead of 6-monodeoxy-6-monoamino-β-cyclodextrin hydrochloride. Reagent 7 was isolated as a white solid. m/z $[M+2H]^{2+}$ (1740, 30%), $[M+3H]^{3+}$ (1160, 100%).

Example 4: Synthesis of Conjugation Reagent 8 Comprising amido-3'-α-cyclodextrin and the Auristatin Cytotoxic Payload, MMAE

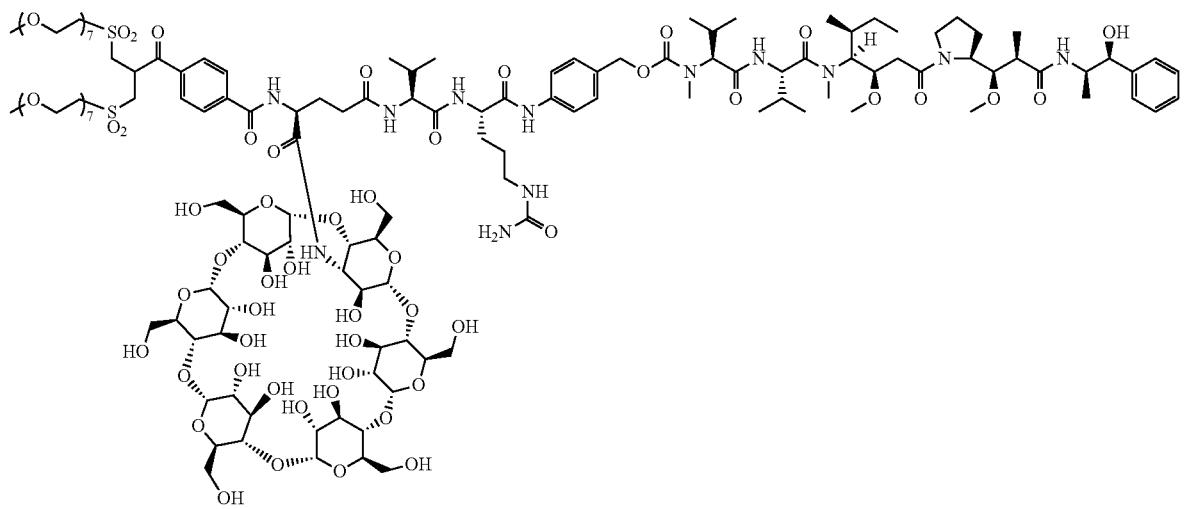

8

Reagent 8 was synthesised in an analogous way to reagent 1 of Example 1 using 3-monodeoxy-3-monoamino-α-cyclodextrin hydrate instead of 6-monodeoxy-6-monoamino-3-cyclodextrin hydrochloride. Reagent 8 was isolated as a white solid. m/z [M+2H]$^{2+}$ (1578, 90%), [M+3H]$^{3+}$ (1052, 100%).

Example 5: Synthesis of Conjugation Reagent 9 Comprising amido-3'-γ-cyclodextrin and the Auristatin Cytotoxic Payload, MMAE

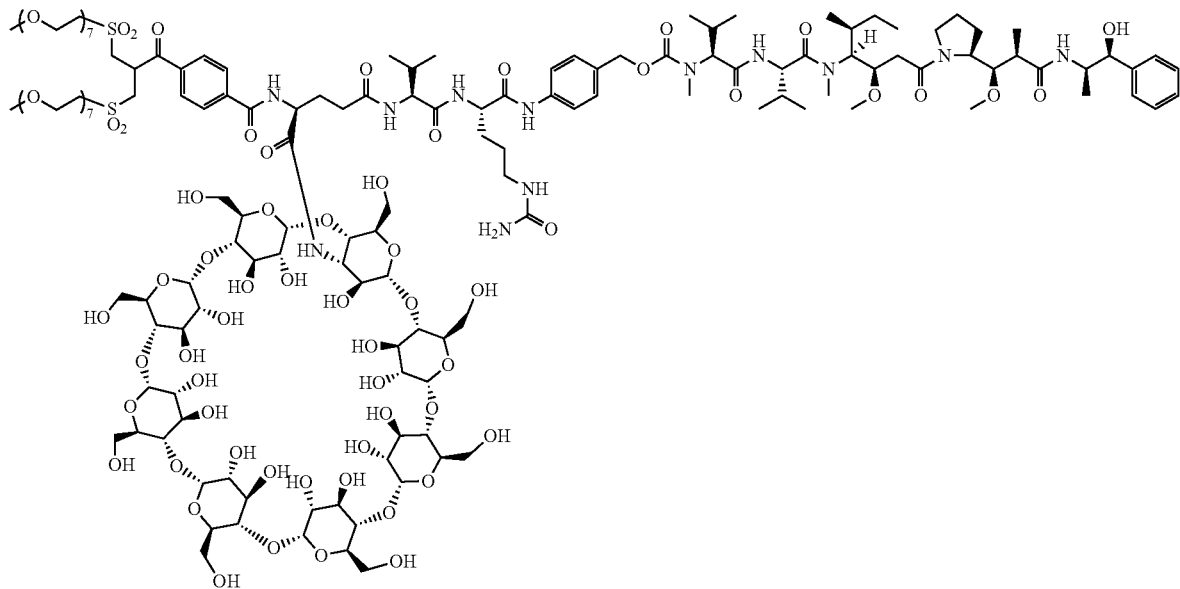

Reagent 9 was synthesised in an analogous way to reagent 1 of Example 1 using 3-monodeoxy-3-monoamino-γ-cyclodextrin hydrate instead of 6-monodeoxy-6-monoamino-3-cyclodextrin hydrochloride. Reagent 9 was isolated as a white solid. m/z [M+2H]$^{2+}$ (1740, 40%), [M+3H]$^{3+}$ (1160, 100%).

Example 6: Synthesis of Conjugation Reagent 10 Comprising amido-3'β-cyclodextrin and the Auristatin Cytotoxic Payload, MMAE

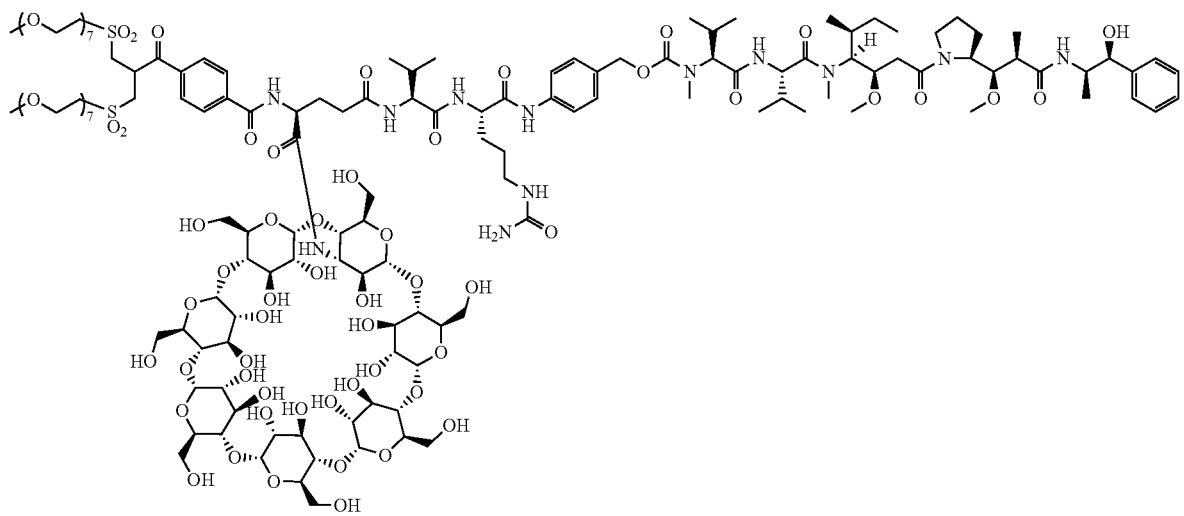

Reagent 10 was synthesised in an analogous way to reagent 1 of Example 1 using 3-monodeoxy-3-monoamino-3-cyclodextrin hydrate instead of 6-monodeoxy-6-mono-amino-3-cyclodextrin hydrochloride. Reagent 10 was isolated as a white solid. m/z [M+2H]$^{2+}$ (1658, 90%).

Example 7: Synthesis of Conjugation Reagent 11 Comprising amido-6'β-cyclodextrin and a Maytansinoid Cytotoxic Payload

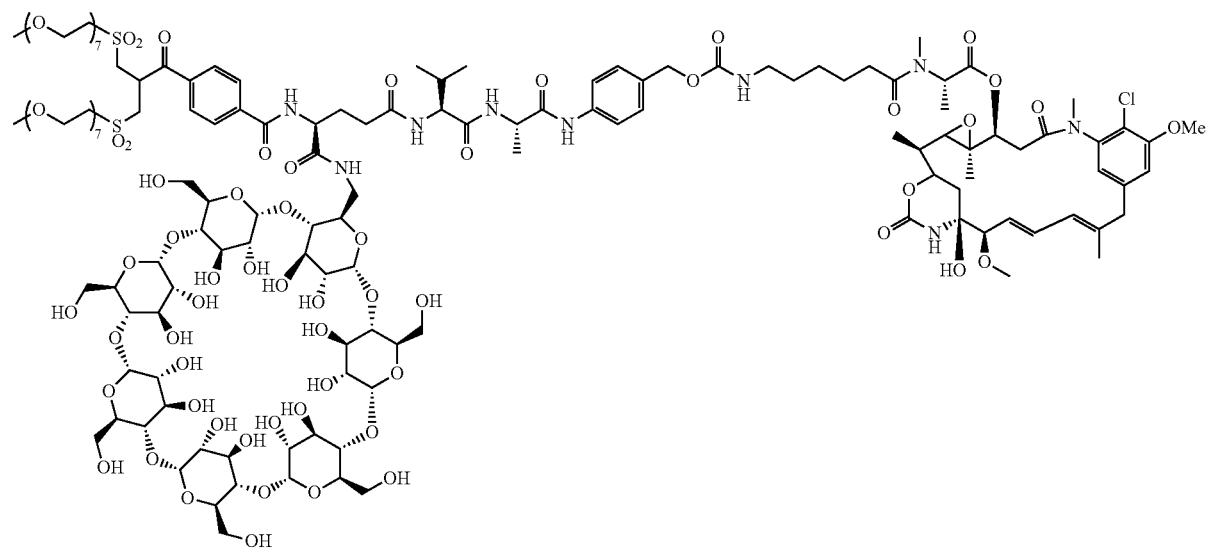

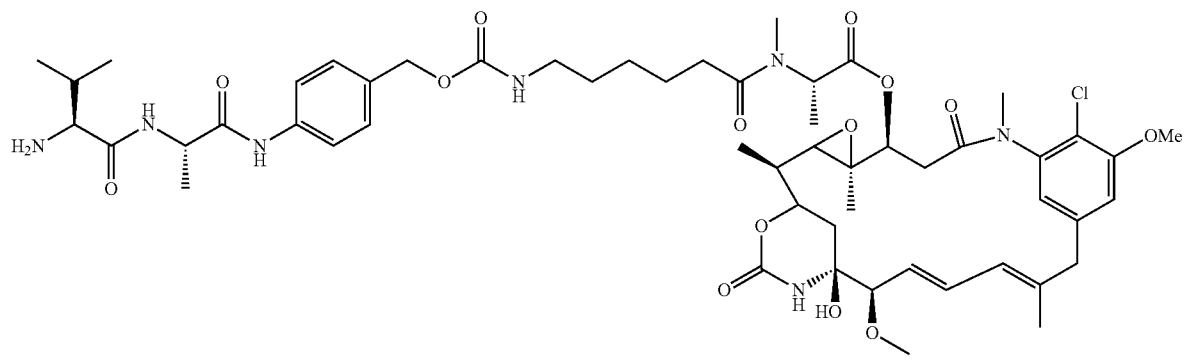

Val-Ala-PAB—AHX—DM1

Step 1: Synthesis of Compound 12.

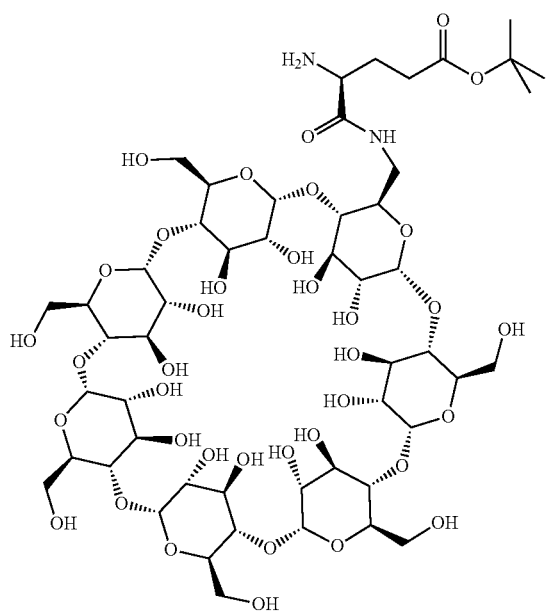

12

To a solution of Fmoc-Glu-(OtBu)-OH (55 mg) in DMF (1 mL) was added a solution of HATU (116 mg) in DMF (1 mL), NMM (34 µl) and a solution of 6-monodeoxy-6-monoamino-β-cyclodextrin hydrochloride (150 mg) in DMF (2 mL). After stirring the reaction mixture for 16 h at room temperature, NMM (13 µl) was added followed after a further 1 h by additional 6-monodeoxy-6-monoamino-β-cyclodextrin hydrochloride (8 mg) in DMF (200 After 3 h, the volatiles were removed in vacuo. The residue was dissolved in DMF (5 mL) and piperidine (151 µL) was added to the solution which was stirred for 1 h at room temperature. The reaction solution was then concentrated in vacuo and the resultant oil precipitated into diethyl ethyl (4×200 mL) at room temperature and filtered to give compound 12 as a white solid. m/z [M+H]⁺ (1320, 50%).

Step 2: Synthesis of Compound 13.

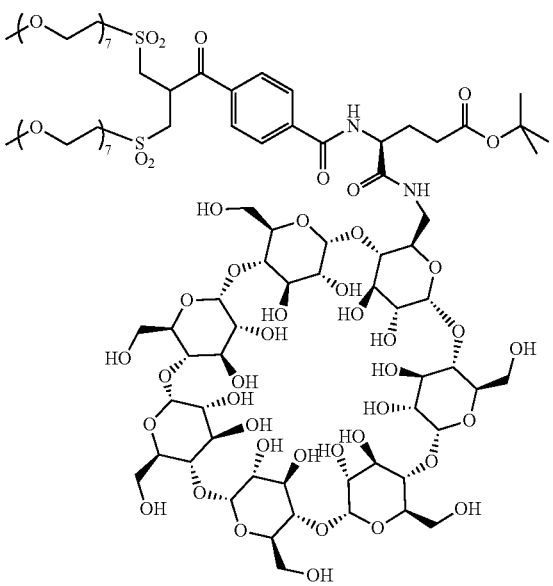

13

To a solution of reagent 5 (156 mg) in DMF (2 mL) was added a solution of HATU (141 mg) in DMF (1 mL), NMM (41 µl) and a solution of compound 12 (196 mg) in DMF (2.5 mL). After stirring for 2.5 h at 0° C., additional reagent 5 (19 mg) in DMF (500 µl) was added. After 20 min, the solution was concentrated in vacuo and the residue purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give compound 13 as a colourless oil (76 mg). m/z [M+H]⁺ (2267, 20%), [M+2H]²⁺ (1134, 100%).

Step 3: Synthesis of Compound 14.

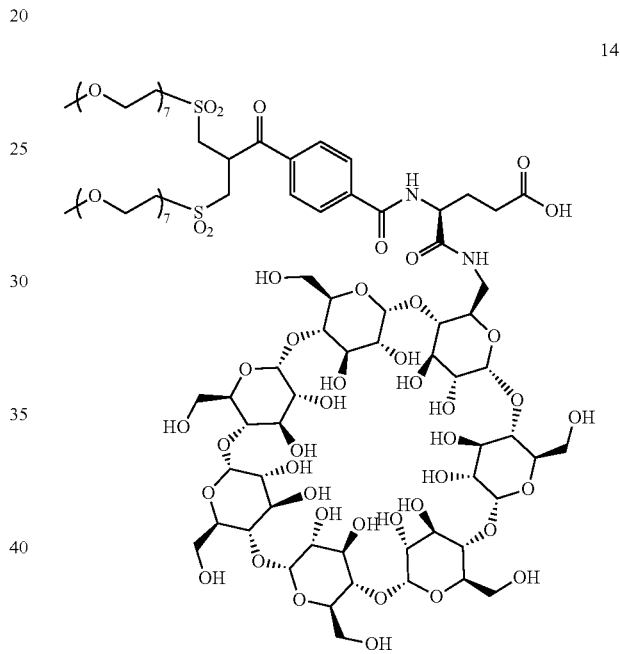

14

To a solution of compound 13 (33 mg) in THF:chloroform (5 mL, 1:4 v/v) was added p-toluenesulfonic acid (14 mg) and the resulting suspension was stirred at room temperature. After 3.5 hours, the volatiles were removed in vacuo and the resulting residue was purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give compound 14 as a colourless oil (26 mg). m/z [M+H]⁺ (2212, 25%), [M+2H]²⁺ (1106, 100%).

Step 4: Synthesis of Reagent 11.

To a stirred solution of compound 14 (18 mg) in DMF (250 µL) under an inert argon atmosphere at room temperature was added HATU (6 mg). After 1 h, additional HATU (6 mg) and NMM (1.1 µL) was added and the solution left to stir for a further 0.5 h. A separate solution of Val-Ala-PAB-AHX-DM1.TFA salt (Levena Biopharma, 7.5 mg) and NMM (1.7 µL) in DMF (100 µL) was prepared and stirred for 20 min at room temperature before the two solutions were combined. Additional HATU (6 mg) and NMM (1.7 μL) were added and the solution was stirred at room temperature. After 2 h, additional HATU (6 mg) was added and the solution was left to stir for a further 4 h at room temperature before additional NMM (1.7 μL) was added. After 3.5 h, the volatiles were removed in vacuo and the resulting residue purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 11 (2.7 mg). m/z $[M+Na+2H]^{3+}$ (1100, 65%). $[M+3H]^{3+}$ (1094, 100%).

Example 8: Synthesis of Conjugation Reagent 15 Comprising amido-6'β-cyclodextrin and a Duocarmycin Cytotoxic Payload

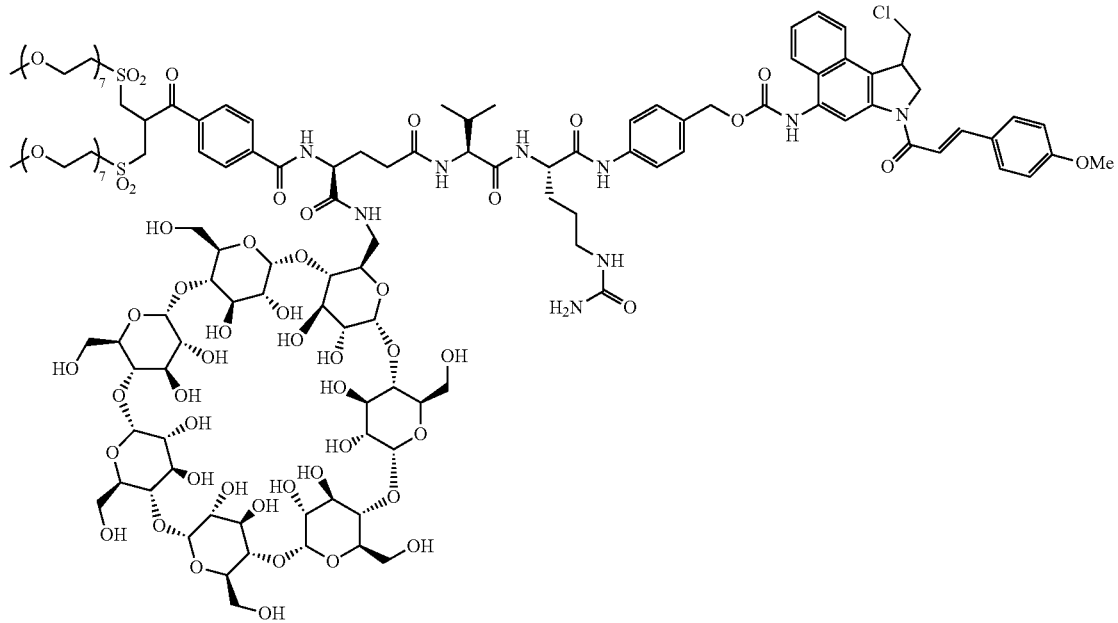

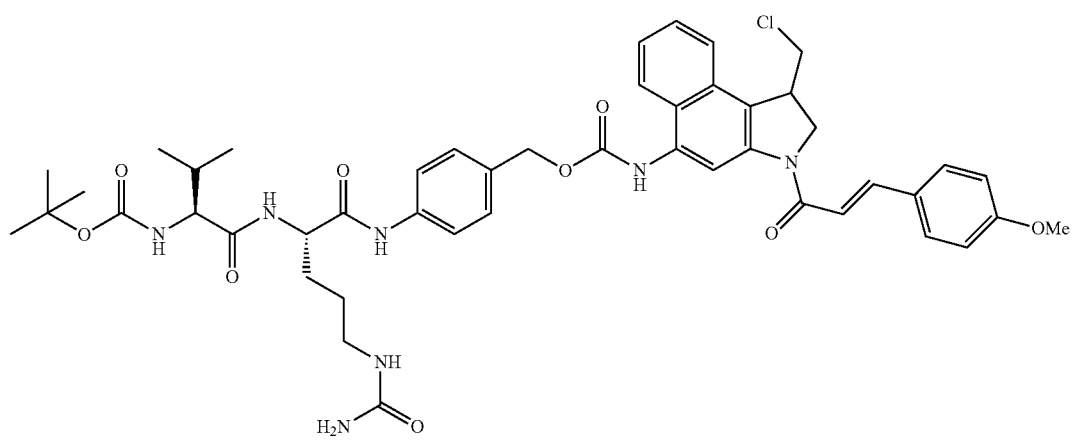

Boc-Val-Cit-PAB-Duocarmycin

Step 1: Synthesis of Compound 16.

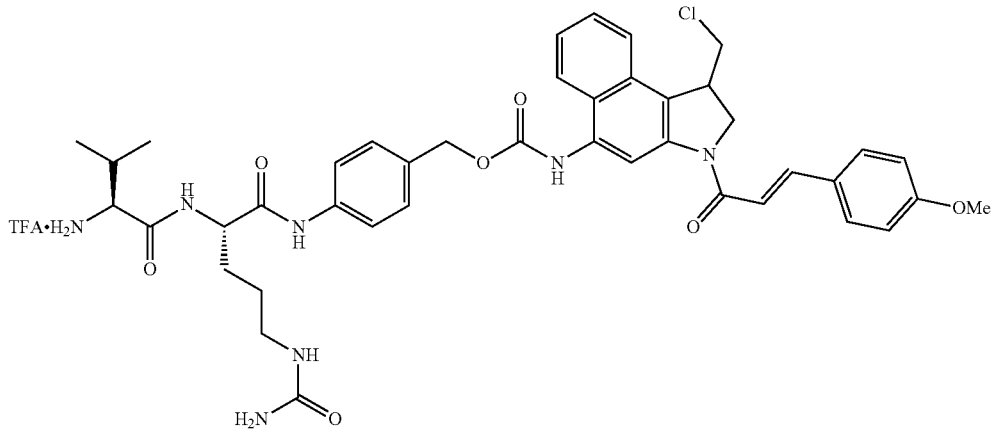

To a suspension of Boc-Val-Cit-PAB-Duocarmycin (Abzena, TCRS, 17 mg) in anhydrous dichloromethane (2 mL) at 0° C. was added trifluoroacetic acid (1 mL) and the resulting solution was stirred at 0° C. for 75 min. The volatiles were then removed in vacuo to give compound 16 as a yellow solid (assumed quantitative yield, 17.7 mg). m/z [M+H]$^+$ (798, 100%).

Step 2: Synthesis of Compound 17.

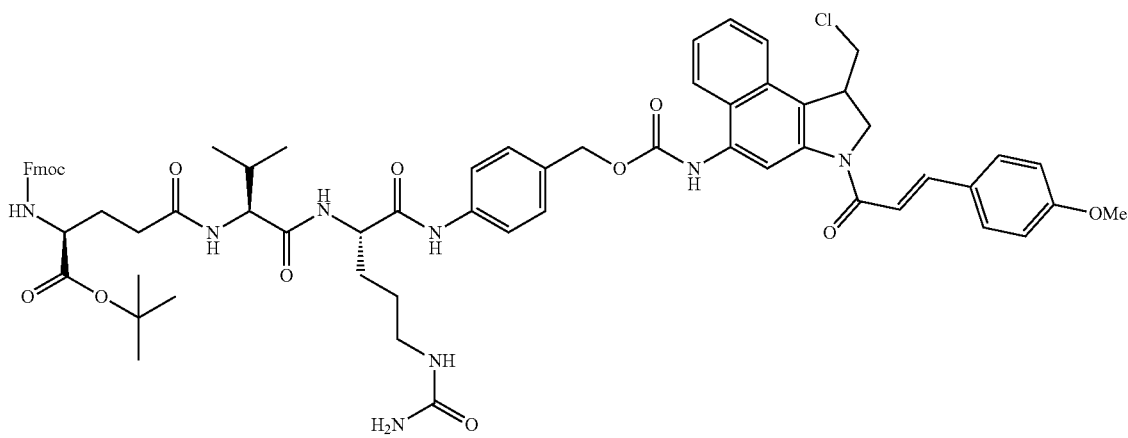

To a stirred solution of compound 16 (17.7 mg, assumed quantitative yield from previous step) in DMF (600 μL) was added a solution of Fmoc-Glu(OH)-OtBu (9 mg) in DMF (200 μL). HATU (22 mg) was added to the reaction mixture which was cooled to 0° C. before NMM (6.4 μL) was added. After 20 min, the reaction mixture was warmed to room temperature and stirred for 50 min before additional HATU (22 mg) and NMM (6.4 μL) were added. After 30 min, the reaction mixture was purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The solvent was removed by lyophilisation to give compound 17 as a yellow solid (assumed quantitative yield, 23.4 mg). m/z [M+H]$^+$ (1206, 5%).

Step 3: Synthesis of Compound 18.

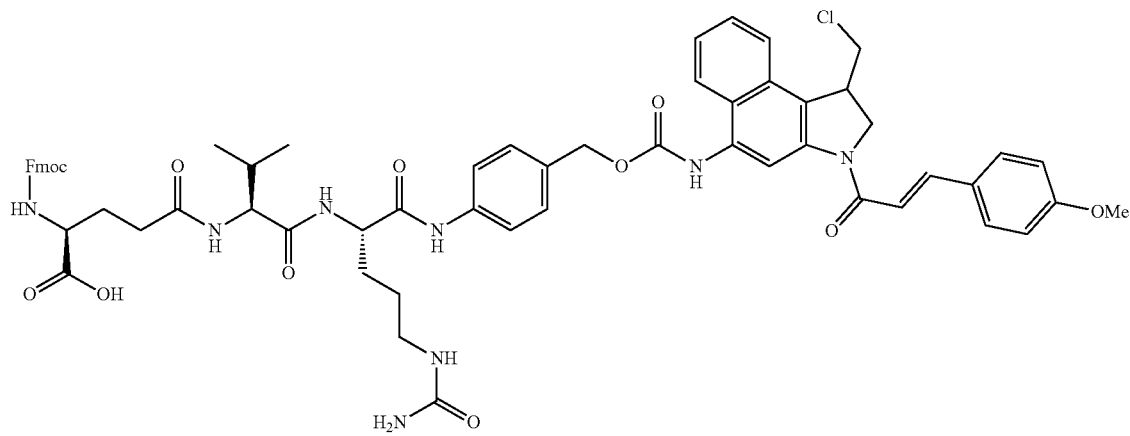

18

Compound 17 (assumed quantitative yield from previous step) was dissolved in a solution of dichloromethane:trifluoroacetic acid (2.5 mL 2:1 v/v). The solution was placed at 4° C. for 5.5 h before being stored at −20° C. for 17 h. The solution was concentrated in vacuo and the residue purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The solvent was removed by lyophilisation to give compound 18 as a yellow solid (3 mg). m/z [M+H]$^+$ (1149, 100%).

Step 4: Synthesis of Compound 19.

To a solution of compound 18 (3 mg) in DMF (220 μL) was added 6-monodeoxy-6-monoamino-β-cyclodextrin hydrochloride (3.7 mg) and HATU (3 mg). The stirred solution was cooled to 0° C. before NMM (0.9 μL) was added. After 30 min, the solution was allowed to warm to room temperature before piperidine (2.6 μL) was added and the reaction mixture stirred for 3.5 h at room temperature. The reaction mixture was then purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The

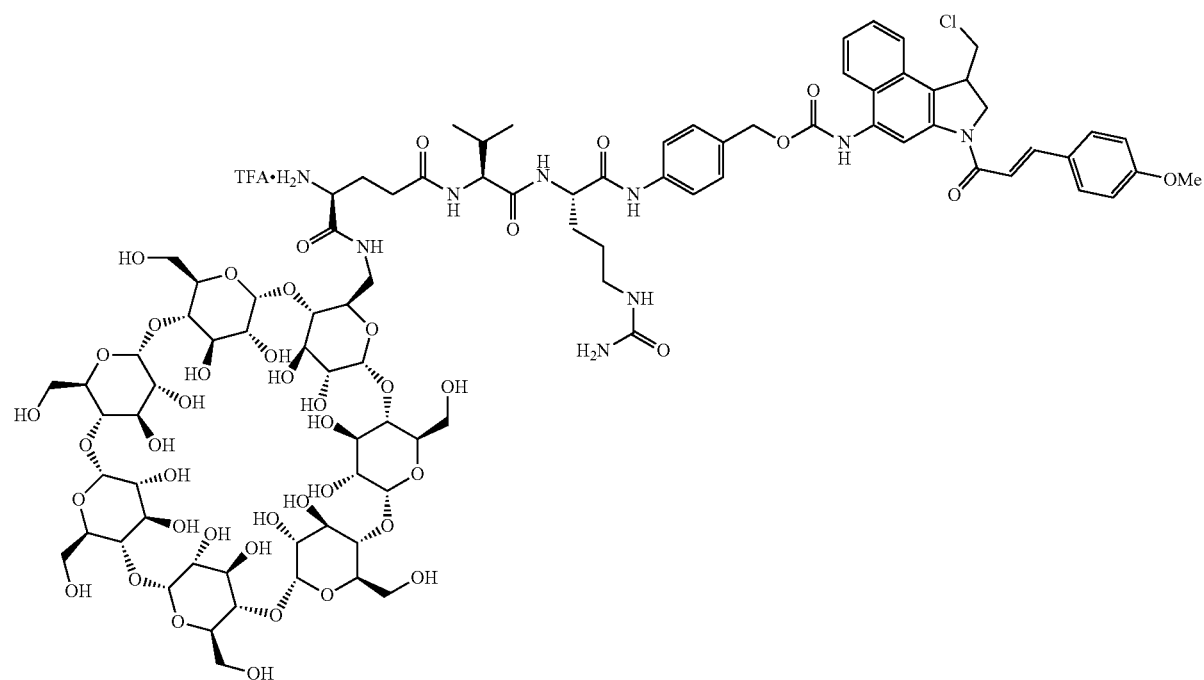

19 solvent was removed by lyophilisation to give compound 19 as a yellow solid (6.3 mg). m/z [M+2H]$^{2+}$ (1022, 100%).
Step 5: Synthesis of Reagent 15.

To a solution of compound 19 (6 mg) in DMF (400 µL) was added reagent 5 (3 mg) and HATU (3.3 mg). The stirred solution was cooled to 0° C. before NMM (1 µL) was added. After 1 h, additional HATU (0.6 mg) and NMM (0.2 µL) were added to the reaction mixture which was stirred for a further 30 min. The reaction mixture was then purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The solvent was removed by lyophilisation to give reagent 15 as a yellow solid (3.7 mg). m/z [M+2H]$^{2+}$ (1495, 100%), [M+Na+2H]$^{3+}$ (1005, 30%).

Example 9: General Protocol for Conjugation of Reagents to Antibodies to Produce Antibody Drug Conjugates (ADCs) with DAR 4

Antibody at a concentration of 5.2 mg/mL in 20 mM sodium phosphate, pH 7.5 (containing 150 mM NaCl and 20 mM EDTA) was heated to 40° C. in a heating block for 15 min. TCEP (6 eq. per mAb) was added to the mAb solution, mixed gently and incubated at 40° C. for 1 h before being allowed to cool to 22° C. Conjugation reagents 1, 6, 7, 8, 9, 10, 11 and 15 were dissolved in DMF to give 1.5 mM solutions. The reduced mAb solution was diluted to 4.4 mg/mL with 20 mM sodium phosphate, pH 7.5 (containing 150 mM NaCl and 20 mM EDTA). Conjugation reagents (5.6 eq. per mAb) were added to the mAb solution, the reaction was mixed gently and incubated at 22° C. for 6 to 22 h. After this the reaction was treated with 50 mM N-acetyl-L-cysteine (20 eq. over reagent) at 22° C. for 1 h. The crude conjugation mixture was analysed by hydrophobic interaction chromatography. The crude reaction was mixed with an equal volume of 50 mM sodium phosphate, pH 7 (4 M NaCl) and the resulting solution was loaded onto a ToyoPearl Phenyl-650S HIC column equilibrated with 50 mM sodium phosphate, pH 7 (2 M NaCl). The ADC was eluted from the column with a gradient of 50 mM sodium phosphate, pH 7 (20% isopropanol). Fractions containing DAR 4 ADC were pooled and concentrated (Vivaspin 20, 10 kDa PES membrane). The concentrated sample was buffer exchanged into PBS, pH 7.1-7.5 and sterile filtered (0.22 µm PVDF membranes). DAR assignments were based on A248/A280 absorption ratios. The average DAR of conjugates was calculated from the relative peak areas of individual DAR species following HIC analysis at 280 nm. Conjugation of brentuximab antibody with conjugation reagents 1, 6, 7, 8, 9, 10 and 15 produced DAR 4 conjugates 20, 21, 22, 23, 24, 25 and 26 respectively. Conjugation of anti-PSMA antibody with reagent 11 produced the DAR 4 conjugate 27.

Example 10: Analysis of Antibody Drug Conjugates (ADCs) by In Vitro Cell Viability Assay The in vitro efficacy of the antibody drug conjugates 20, 21, 22, 23, 24, 25, 26 and 27 prepared in Example 9 was determined by measuring their inhibitory effect upon cell growth of a target over-expressing cancer cell line.

Loss of tumour cell viability following treatment with ADCs or free payloads in vitro can be measured by growing cell lines in the presence of increasing concentrations of compounds and quantifying the loss of proliferation or metabolic activity using Cell-Titer Glo® Luminescent reagent (Promega). The protocol describes cell seeding, drug treatment and determination of the cell viability in reference to untreated cells based on ATP synthesis, which is directly correlated to the number of cells present in the well.

The characteristics of the cell line as well as the seeding densities for the assays are described in the table below. We acknowledge Dr. Karpas for provision of the Karpas-299 cell line. Cells were counted using disposable Neubauer counting chambers and cell density adjusted as detailed in the table below. Karpas-299 and LNCaP cells were seeded at 50 µL/well into Tissue Culture treated opaque-walled 96-well white plates and incubated for 24 h at 37° C. and 5% $CO_2$.

| Cell line | Target | Growth Medium | Seeding density |
|---|---|---|---|
| Karpas-299 | CD30 | RPMI-1640 medium (Life Technologies ®), 10% fetal bovine serum, 100 U/mL Penicillin and 100 µg/mL Streptomycin | 0.25 × 10$^4$ cells per well |
| LNCaP clone FGC | PSMA | | 1 × 10$^4$ cells per well |

Eight point serial dilutions of compounds were prepared in the relevant culture medium. The titration range was adjusted for each compound/cell line combination. Karpas-299 cells were treated by simple addition of 50 µL/well of 2×ADC dilutions. For the LNCaP cells, growth medium was removed and replaced by 100 µL/well of 1×ADC dilutions. The cells were then incubated at 37° C. and 5% $CO_2$ for a further 96 h.

The cell viability assay was carried out using the Cell-Titer Glo® Luminescent reagent (Promega), as described by the manufacturer.

Luminescence was recorded using a Molecular Devices SpectramaxM3 plate reader and data subsequently analysed using GraphPad Prism four parameter non-linear regression model. Viability was expressed as % of untreated cells and calculated using the following formula:

$$\% \text{ Viability} = 100 \times \frac{Luminescence_{Sample} - Luminescence_{No\ Cell\ Control}}{Luminescence_{Untreated} - Luminescence_{No\ Cell\ Control}}$$

The % viability was plotted against the logarithm of drug concentration in nM to extrapolate the IC$_{50}$ values for all conjugates.

The results of the in vitro cytotoxicity studies are given in Table 1. These data show that the cyclodextrin ADCs have potent cell killing properties in vitro.

TABLE 1

| Cell line | Compound | IC$_{50}$ |
|---|---|---|
| Karpas-299 | 20 | 28 pM |
| Karpas-299 | 21 | 30 pM |
| Karpas-299 | 22 | 28 pM |
| Karpas-299 | 23 | 14 pM |
| Karpas-299 | 24 | 14 pM |
| Karpas-299 | 25 | 19 pM |
| Karpas-299 | 26 | 106 pM |
| LNCaP | 27 | 1.3 nM |

Example 11: Karpas-299 Mouse Xenograft Studies Comparing Brentuximab-Drug Conjugates 20, 23 and 24 to Adcetris® (Comparative Healthy female CB17-SCID mice (CBySmn.CB17-Prkdcscida, Charles River Laboratories) with an average body weight of 17.5 g were used for cell inoculation (Day 0). 24 to 72 h prior to tumour cell injection, the mice were α-irradiated (1.44 Gy, $^{60}$Co). The animals were maintained in SPF health status according to the FELASA guidelines in housing rooms under controlled environmental conditions.

Tumours were induced by subcutaneous injection of $10^7$ Karpas-299 cells (T-anaplastic large cell lymphoma, ALCL) in 200 µL of RPMI 1640 into the right flank. Tumours were measured twice a week with callipers, and the volume was estimated using the formula:

$$\text{Tumour Volume (mm}^3) = \frac{\text{width}^2 \times \text{length}}{2}$$

Fourteen days after tumour implantation (Day 14), the animals were randomised into groups of eight mice using Vivo Manager® software (233 mm³ mean tumour volume) and treatment was initiated. The animals from the vehicle group received a single intravenous (i.v.) injection of PBS. The treated groups were dosed with a single i.v. injection of ADC at either 0.5 mg/kg or 1 mg/kg.

Treatment tolerability was assessed by bi-weekly body weight measurement and daily observation for clinical signs of treatment-related side effects. Mice were euthanized when a humane endpoint was reached (e.g. 1,600 mm³ tumour volume) or after a maximum of 6 weeks post-dosing.

Figure 2:
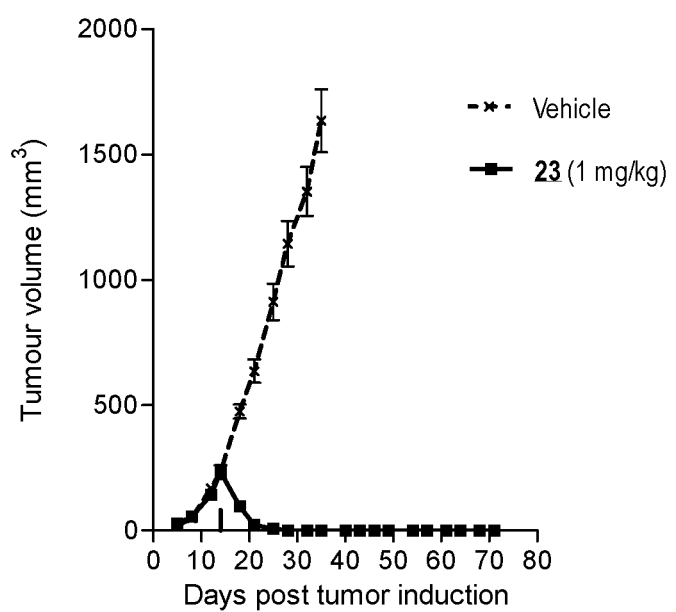
Figure 3:
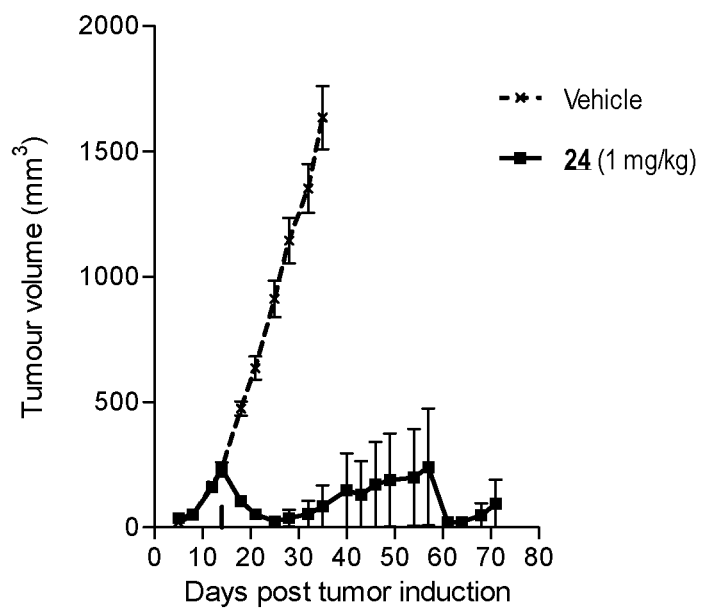
Figure 4:
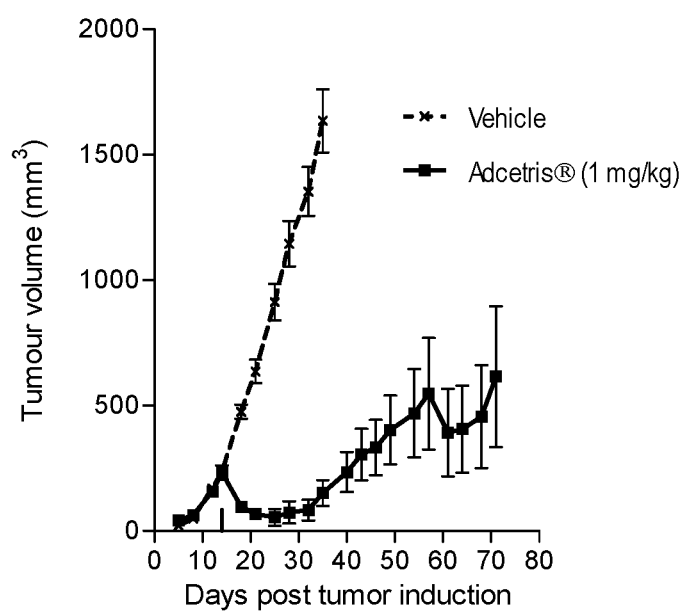

The mean tumour volume±standard error for the 1 mg/kg dose is represented in FIGS. 1 to 4 for each group. All compounds were well tolerated. At this dose, conjugate 20 showed a large reduction in mean tumour volume overall, with complete responses (i.e. total reduction of tumour volume to zero) observed in 6/8 animals which survived the duration of the study. Conjugate 23 showed a total regression in mean tumour volume, with all (8/8) animals surviving the study duration. Conjugate 24 also displayed a large reduction in mean tumour volume with complete responses in 6/8 animals. In contrast, the commercially-available Adcetris® conjugate showed an increase in mean tumour volume throughout the course of the study, with complete responses observed in only 2 animals at the same dose.

Example 12: Stability of Antibody Drug Conjugates (ADCs) by Freeze Thaw Test ADC samples 20, 21, 22, 23, 24 and 25 were each prepared at 0.5 mg/mL by dilution with DPBS pH 7.1-7.5.

The ADC samples were incubated at −80° C. for 1 h before thawing at 4° C. The samples were then analysed by Size Exclusion Chromatography (SEC) using a TOSOH Bioscience TSK gel Super SW 3000 column. UV absorbance at 280 nm was monitored during an isocratic elution with a 0.2 M potassium phosphate buffer, pH 6.8 (0.2 M potassium chloride and 15% isopropanol).

Table 2 shows the extent of aggregation of the ADCs following the freeze thaw test. The percentage area under the curve (Abs 280) derived from SEC analysis, was used to determine the quantity of aggregated species present within each sample.

TABLE 2

| Compound | Change in aggregate peak area (%) after freeze thaw test |
|---|---|
| 20 | 1.9 |
| 21 | 8.7 |
| 22 | 1.7 |
| 23 | 0.9 |
| 24 | 4.2 |
| 25 | 1.8 |

These data in Table 2 show that each of the conjugates display good stability following freezing and thawing of the samples.

The invention claimed is:

1. A conjugate of a protein or peptide conjugated to a therapeutic agent via a linker, in which the linker also includes a cyclodextrin, and in which the cyclodextrin is present as a pendant group which is tethered to the backbone of the linker, wherein the conjugate is represented schematically by the formula:

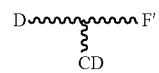

in which:
D represents said therapeutic agent,
F' represents a group of formula I:

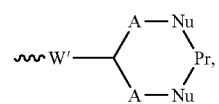

in which Pr represents said protein or peptide, each Nu represents a sulfur atom or amine group present in or attached to the protein or peptide, each of A and B independently represents a $C_{1-4}$ alkylene or alkenylene chain, and W' represents a keto group —CO—, an ester group —O—CO—, a sulfone group —SO$_2$—, or a group obtained by reduction of one of these groups; and CD represents said cyclodextrin.

2. A conjugate as claimed in claim 1, in which the cyclodextrin is α-cyclodextrin, β-cyclodextrin, or γ-cyclodextrin.

3. A conjugate as claimed in claim 1, in which the cyclodextrin is bonded to the rest of the linker via the 3- or the 6-position of a cyclic glucose group.

4. A conjugate as claimed in claim 1, in which the cyclodextrin is monocyclic.

5. A conjugate as claimed in claim 1, in which the linker includes a portion

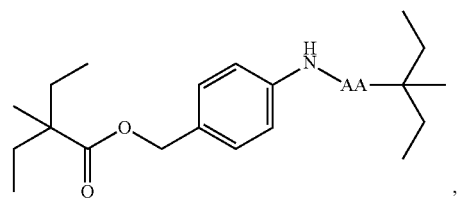

wherein AA represents a protease-specific amino acid sequence.

6. A conjugate as claimed in claim 1, in which the protein or peptide is an antibody or an antibody fragment.

7. A conjugate as claimed in claim 1, wherein the group of formula (I) is a group of formula (Ia):

(Ia)

8. A conjugate as claimed in claim 7, wherein the group of formula (Ia) is a group of formula (Ib) or (Ic):

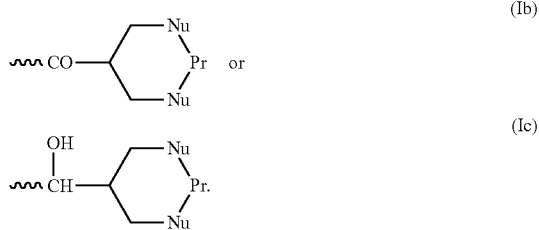

9. A conjugate as claimed in claim 1, in which each Nu represents a sulfur atom present in a cysteine residue present in the protein or peptide.

10. A conjugate as claimed in claim 1, which has the formula:

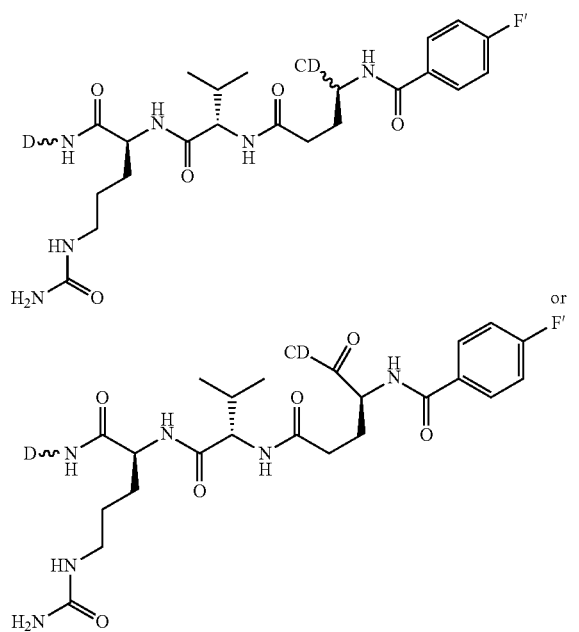

11. A process for the preparation of a conjugate as claimed in claim 1, which comprises reacting a protein or peptide with a conjugating reagent comprising a therapeutic agent and a linker in which the linker also includes a cyclodextrin, and in which the cyclodextrin is present as a pendant group which is tethered to the backbone of the linker, wherein the conjugate reagent is represented schematically by the formula:

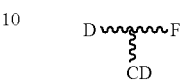

in which: D represents said therapeutic agent,
CD represents said cyclodextrin, and
F is capable of reacting with sulfur atom or amine group present in or attached to the protein or peptide and F represents a group of formula (II) or (II'):

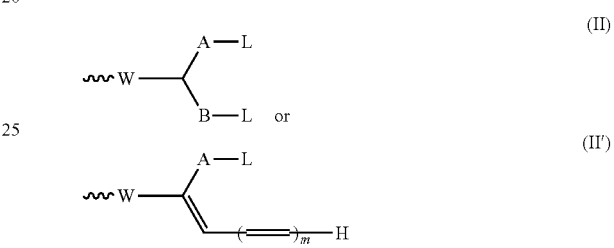

in which W represents a keto group —CO, an ester group —O—CO—, or a sulfone group —$SO_2$—;
each of A and B independently represents a $C_{1-4}$alkylene, or alkenylene chain, m is 0 to 4, and
each L independently represents a leaving group selected from —SP, —OP, —$SO_2$P, —$OSO_2$P, —$N^+PR^2R^3$, halogen, or —OØ, in which P represents a hydrogen atom, $C_{1-6}$alkyl, phenyl, or $C_{1-6}$alkyl-phenyl group, or is a group which includes a portion —$(CH_2CH_2O)_n$— in which n is a number of two or more, and each of $R^2$ and $R^3$ independently represents a hydrogen atom, a $C_{1-4}$alkyl group, or a group P, and Ø represents a substituted phenyl, group, containing at least one substituent selected from the group consisting of —CN, —$NO_2$, —$CF_3$, —$CO_2R^a$, —COH, —$CH_2OH$, —$COR^a$, —$OR^a$, —$OCOR^a$, —$OCO_2R^a$, —$SR^a$, —$SOR^a$, —$SO_2R^a$, —$NR^aCOR^a$, —$NR^aCO_2R^a$, —NO, —NHOH, —$NR^a$OH, —CH=N—$NR^a$ $COR^a$, —$N^+R^a_3$, halogen, —CH=$CR^a$, and —C≡$CR^a_2$ in which each $R^a$ represents a hydrogen atom, $C_{1-6}$alkyl, phenyl, or $C_{1-6}$alkyl-phenyl group.

12. A pharmaceutical composition which comprises a conjugate as claimed in claim 1 together with a pharmaceutically acceptable carrier, and optionally together with a further active ingredient.

13. A conjugate as claimed in claim 1, in which the therapeutic agent is an auristatin, a maytansinoid or a duocarmycin.

* * * * *

UNITED STATES PATENT AND TRADEMARK OFFICE
CERTIFICATE OF CORRECTION

PATENT NO. : 11,027,022 B2  Page 1 of 1
APPLICATION NO. : 16/097864
DATED : June 8, 2021
INVENTOR(S) : Antony Godwin It is certified that error appears in the above-identified patent and that said Letters Patent is hereby corrected as shown below:

In the Claims

Claim 11, Column 52, Line 43, "phenyl, group" should read -- phenyl group --
Claim 11, Column 52, Line 49, "-CH≡CR$^a$" should read -- -C≡CR$^a$ --
Claim 11, Column 52, Line 49, "-C=CR$^a_2$" should read -- -CH=CR$^a_2$ --

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*